(12) United States Patent
Buist et al.

(10) Patent No.: US 7,402,563 B2
(45) Date of Patent: Jul. 22, 2008

(54) EPF DERIVED PEPTIDES AND THERAPEUTIC COMPOSITIONS

(75) Inventors: Arjan Buist, Beerse (BE); Eckhard Bender, Beerse (BE); Tom J. L. Meeusen, Leuven (BE); Elke J. H. Clynen, Leuven (BE); Liliane A. H. Schoofs, Leuven (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 11/387,009

(22) Filed: Mar. 22, 2006

(65) Prior Publication Data

US 2006/0160145 A1 Jul. 20, 2006

Related U.S. Application Data

(63) Continuation of application No. 10/481,161, filed as application No. PCT/EP02/07263 on Jun. 26, 2002, now abandoned.

(51) Int. Cl.
*C07K 7/08* (2006.01)
*A01N 37/18* (2006.01)
*C12N 15/12* (2006.01)

(52) U.S. Cl. .......................... 514/2; 435/69.1; 530/326; 536/23.5

(58) Field of Classification Search ................. None
See application file for complete search history.

(56) References Cited

FOREIGN PATENT DOCUMENTS

| WO | WO 95/15339 | 6/1995 |
|----|-------------|--------|
| WO | WO 97/18309 | 5/1997 |
| WO | WO 99/32519 | 7/1999 |
| WO | WO 01/36471 A2 | 5/2001 |
| WO | WO 01/19983 A1 | 3/2003 |

OTHER PUBLICATIONS

Lembo et al., Proenkephalin A Gene Products Activate a New Family of Sensory Neuron-Specific GPCRs, Mar. 2002, Nature neuroscience 5(3):201-209.*
Morton et al., Production of a Recombinant Form of Early Pregnancy Factor That Can Prolong Allogeneic Skin GraftSurvival Time in Rats, 2000, Immunology and Cell Biology 78:603-607.*
Database EMBL Online "Heat Shock Protein 10 (Cpn10, groES)", *Database accession No. 042283.*
Jarvis, Jackie A. et al., "Solution Structure of the Acetylated and Noncleavable Mitochondrial Targeting Signal of Rat Chaperonin 10", *J. Biol. Chem.*, 270:1323-1331 (1995).
Database EMBL 1998, "ok82f05.s1 NCI_CGAP_Kid3 *Homo sapiens* cDNA clone Image: 1520481 3' similar to SW:CH10_Human Q04984 10 KD Heat Shock Protein, Mitochondrial;, mRNA sequence", Database accession No. AA923068.
Maria J. Somodevilla-Torres et al., "Preparation and characterization of polyclonal antibodies against human chaperonin 10", Cell Stress & Chaperones (2000)5, (1), pp. 14-20.

* cited by examiner

*Primary Examiner*—John Ulm
(74) *Attorney, Agent, or Firm*—Woodcock Washburn LLP

(57) ABSTRACT

The present invention provides assays for the study of the interaction of EPF and its EPF-related peptides with a hDRR receptor. The assays are useful to identify whether a test compound can bind to the hDRR receptor under conditions in which EPF or related peptide can bind to the receptor. The assays are also useful to determine whether the test compound is an agonist or antagonist of hDRRs. The above assays can be performed in a variety of formats including competitive, non-competitive and comparative assays in which the interaction of EPF or EPF-related peptides with hDRRs is assessed as a positive or negative control or compared to the results obtained with the test compound.

5 Claims, 7 Drawing Sheets

Fig.1.A

>hDRR4

ATGGATCCAACCATCTCAACCTTGGACACAGAACTGACACCAATCAACGGAACTGAGGAGACTCTTTGCT
ACAAGCAGACCTTGAGCCTCACGGTGCTGACGTGCATCGTTTCCCTTGTCGGGCTGACAGGAAACGCAGT
TGTGCTCTGGCTCCTGGGCTGCCGCATGCGCAGGAACGCCTTCTCCATCTACATCCTCAACTTGGCCGCA
GCAGACTTCCTCTTCCTCAGCGGCCGCCTTATATATTCCCTGTTAAGCTTCATCAGTATCCCCCATACCA
TCTCTAAAATCCTCTATCCTGTGATGATGTTTTCCTACTTTGCAGGCCTGAGCTTTCTGAGTGCCGTGAG
CACCGAGCGCTGCCTGTCCGTCCTGTGGCCCATCTGGTACCGCTGCCACCGCCCCACACACCTGTCAGCG
GTGGTGTGTGTCCTGCTCTGGGCCCTGTCCCTGCTGCGGAGCATCCTGGAGTGGATGTTATGTGGCTTCC
TGTTCAGTGGTGCTGATTCTGCTTGGTGTCAAACATCAGATTTCATCACAGTCGCGTGGCTGATTTTTTT
ATGTGTGGTTCTCTGTGGGTCCAGCCTGGTCCTGCTGATCAGGATTCTCTGTGGATCCCGGAAGATACCG
CTGACCAGGCTGTACGTGACCATCCTGCTCACAGTACTGGTCTTCCTCCTCTGTGGCCTGCCCTTTGGCA
TTCAGTTTTTCCTATTTTTATGGATCCACGTGGACAGGGAAGTCTTATTTTGTCATGTTCATCTAGTTTC
TATTTTCCTGTCCGCTCTTAACAGCAGTGCCAACCCCATCATTTACTTCTTCGTGGGCTCCTTTAGGCAG
CGTCAAAATAGGCAGAACCTGAAGCTGGTTCTCCAGAGGGCTCTGCAGGACGCGTCTGAGGTGGATGAAG
GTGGAGGGCAGCTTCCTGAGGAAATCCTGGAGCTGTCGGGAAGCAGATTGGAGCAGTGA

Fig.1.B

>hDRR4

MDPTISTLDTELTPINGTEETLCYKQTLSLTVLTCIVSLVGLTGNAVVLWLLGCRMRRNAFSIYILNLAA
ADFLFLSGRLIYSLLSFISIPHTISKILYPVMMFSYFAGLSFLSAVSTERCLSVLWPIWYRCHRPTHLSA
VVCVLLWALSLLRSILEWMLCGFLFSGADSAWCQTSDFITVAWLIFLCVVLCGSSLVLLIRILCGSRKIP
LTRLYVTILLTVLVFLLCGLPFGIQFFLFLWIHVDREVLFCHVHLVSIFLSALNSSANPIIYFFVGSFRQ
RQNRQNLKLVLQRALQDASEVDEGGGQLPEEILELSGSRLEQ*

SEQUENCE LISTING

<160> NUMBER OF SEQ ID NOS: 24

<210> SEQ ID NO 1
<211> LENGTH: 969
<212> TYPE: DNA
<213> ORGANISM: Homo sapiens
<220> FEATURE:
<221> NAME/KEY: CDS
<222> LOCATION: (1)..(966)
<223> OTHER INFORMATION:

<400> SEQUENCE: 1

```
atg gat cca acc atc tca acc ttg gac aca gaa ctg aca cca atc aac      48
Met Asp Pro Thr Ile Ser Thr Leu Asp Thr Glu Leu Thr Pro Ile Asn
1               5                   10                  15 gga act gag gag act ctt tgc tac aag cag acc ttg agc ctc acg gtg      96
Gly Thr Glu Glu Thr Leu Cys Tyr Lys Gln Thr Leu Ser Leu Thr Val
            20                  25                  30 ctg acg tgc atc gtt tcc ctt gtc ggg ctg aca gga aac gca gtt gtg     144
Leu Thr Cys Ile Val Ser Leu Val Gly Leu Thr Gly Asn Ala Val Val
        35                  40                  45 ctc tgg ctc ctg ggc tgc cgc atg cgc agg aac gcc ttc tcc atc tac     192
Leu Trp Leu Leu Gly Cys Arg Met Arg Arg Asn Ala Phe Ser Ile Tyr
    50                  55                  60 atc ctc aac ttg gcc gca gca gac ttc ctc ttc ctc agc ggc cgc ctt     240
Ile Leu Asn Leu Ala Ala Ala Asp Phe Leu Phe Leu Ser Gly Arg Leu
65                  70                  75                  80 ata tat tcc ctg tta agc ttc atc agt atc ccc cat acc atc tct aaa     288
Ile Tyr Ser Leu Leu Ser Phe Ile Ser Ile Pro His Thr Ile Ser Lys
                85                  90                  95 atc ctc tat cct gtg atg atg ttt tcc tac ttt gca ggc ctg agc ttt     336
Ile Leu Tyr Pro Val Met Met Phe Ser Tyr Phe Ala Gly Leu Ser Phe
            100                 105                 110 ctg agt gcc gtg agc acc gag cgc tgc ctg tcc gtc ctg tgg ccc atc     384
Leu Ser Ala Val Ser Thr Glu Arg Cys Leu Ser Val Leu Trp Pro Ile
        115                 120                 125 tgg tac cgc tgc cac cgc ccc aca cac ctg tca gcg gtg gtg tgt gtc     432
Trp Tyr Arg Cys His Arg Pro Thr His Leu Ser Ala Val Val Cys Val
    130                 135                 140 ctg ctc tgg gcc ctg tcc ctg ctg cgg agc atc ctg gag tgg atg tta     480
Leu Leu Trp Ala Leu Ser Leu Leu Arg Ser Ile Leu Glu Trp Met Leu
145                 150                 155                 160 tgt ggc ttc ctg ttc agt ggt gct gat tct gct tgg tgt caa aca tca     528
Cys Gly Phe Leu Phe Ser Gly Ala Asp Ser Ala Trp Cys Gln Thr Ser
                165                 170                 175 gat ttc atc aca gtc gcg tgg ctg att ttt tta tgt gtg gtt ctc tgt     576
Asp Phe Ile Thr Val Ala Trp Leu Ile Phe Leu Cys Val Val Leu Cys
            180                 185                 190 ggg tcc agc ctg gtc ctg ctg atc agg att ctc tgt gga tcc cgg aag     624
Gly Ser Ser Leu Val Leu Leu Ile Arg Ile Leu Cys Gly Ser Arg Lys
        195                 200                 205
```

-continued

| | | |
|---|---|---|
| ata ccg ctg acc agg ctg tac gtg acc atc ctg ctc aca gta ctg gtc<br>Ile Pro Leu Thr Arg Leu Tyr Val Thr Ile Leu Leu Thr Val Leu Val<br>210                        215                      220 | 672 |
| ttc ctc ctc tgt ggc ctg ccc ttt ggc att cag ttt ttc cta ttt tta<br>Phe Leu Leu Cys Gly Leu Pro Phe Gly Ile Gln Phe Phe Leu Phe Leu<br>225                      230                      235                      240 | 720 |
| tgg atc cac gtg gac agg gaa gtc tta ttt tgt cat gtt cat cta gtt<br>Trp Ile His Val Asp Arg Glu Val Leu Phe Cys His Val His Leu Val<br>                    245                      250                      255 | 768 |
| tct att ttc ctg tcc gct ctt aac agc agt gcc aac ccc atc att tac<br>Ser Ile Phe Leu Ser Ala Leu Asn Ser Ser Ala Asn Pro Ile Ile Tyr<br>        260                      265                      270 | 816 |
| ttc ttc gtg ggc tcc ttt agg cag cgt caa aat agg cag aac ctg aag<br>Phe Phe Val Gly Ser Phe Arg Gln Arg Gln Asn Arg Gln Asn Leu Lys<br>275                        280                      285 | 864 |
| ctg gtt ctc cag agg gct ctg cag gac gcg tct gag gtg gat gaa ggt<br>Leu Val Leu Gln Arg Ala Leu Gln Asp Ala Ser Glu Val Asp Glu Gly<br>290                        295                      300 | 912 |
| gga ggg cag ctt cct gag gaa atc ctg gag ctg tcg gga agc aga ttg<br>Gly Gly Gln Leu Pro Glu Glu Ile Leu Glu Leu Ser Gly Ser Arg Leu<br>305                        310                      315                      320 | 960 |
| gag cag tga<br>Glu Gln | 969 |

<210> SEQ ID NO 2
<211> LENGTH: 322
<212> TYPE: PRT
<213> ORGANISM: Homo sapiens

<400> SEQUENCE: 2

Met Asp Pro Thr Ile Ser Thr Leu Asp Thr Glu Leu Thr Pro Ile Asn
1               5                   10                  15

Gly Thr Glu Glu Thr Leu Cys Tyr Lys Gln Thr Leu Ser Leu Thr Val
            20                  25                  30

Leu Thr Cys Ile Val Ser Leu Val Gly Leu Thr Gly Asn Ala Val Val
        35                  40                  45

Leu Trp Leu Leu Gly Cys Arg Met Arg Arg Asn Ala Phe Ser Ile Tyr
    50                  55                  60

Ile Leu Asn Leu Ala Ala Ala Asp Phe Leu Phe Leu Ser Gly Arg Leu
65                  70                  75                  80

Ile Tyr Ser Leu Leu Ser Phe Ile Ser Ile Pro His Thr Ile Ser Lys
                85                  90                  95

Ile Leu Tyr Pro Val Met Met Phe Ser Tyr Phe Ala Gly Leu Ser Phe
            100                 105                 110

Leu Ser Ala Val Ser Thr Glu Arg Cys Leu Ser Val Leu Trp Pro Ile
        115                 120                 125

Trp Tyr Arg Cys His Arg Pro Thr His Leu Ser Ala Val Val Cys Val
    130                 135                 140

Leu Leu Trp Ala Leu Ser Leu Leu Arg Ser Ile Leu Glu Trp Met Leu
145                 150                 155                 160

Cys Gly Phe Leu Phe Ser Gly Ala Asp Ser Ala Trp Cys Gln Thr Ser
                165                 170                 175

Asp Phe Ile Thr Val Ala Trp Leu Ile Phe Leu Cys Val Val Leu Cys
            180                 185                 190

Gly Ser Ser Leu Val Leu Leu Ile Arg Ile Leu Cys Gly Ser Arg Lys
        195                 200                 205

Ile Pro Leu Thr Arg Leu Tyr Val Thr Ile Leu Leu Thr Val Leu Val

```
                210                 215                 220
Phe Leu Leu Cys Gly Leu Pro Phe Gly Ile Gln Phe Phe Leu Phe Leu
225                 230                 235                 240

Trp Ile His Val Asp Arg Glu Val Leu Phe Cys His Val His Leu Val
                245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Ala Ser Glu Val Asp Glu Gly
    290                 295                 300

Gly Gly Gln Leu Pro Glu Glu Ile Leu Glu Leu Ser Gly Ser Arg Leu
305                 310                 315                 320

Glu Gln

<210> SEQ ID NO 3
<211> LENGTH: 538
<212> TYPE: DNA
<213> ORGANISM: Homo sapiens
<220> FEATURE:
<221> NAME/KEY: CDS
<222> LOCATION: (42)..(347)
<223> OTHER INFORMATION:

<400> SEQUENCE: 3
gctacactag agcagagtac gagtctgagg cggagggagt a atg gca gga caa gcg      56
                                             Met Ala Gly Gln Ala
                                              1               5 ttt aga aag ttt ctt cca ctc ttt gac cga gta ttg gtt gaa agg agt     104
Phe Arg Lys Phe Leu Pro Leu Phe Asp Arg Val Leu Val Glu Arg Ser
                 10                  15                  20 gct gct gaa act gta acc aaa gga ggc att atg ctt cca gaa aaa tct     152
Ala Ala Glu Thr Val Thr Lys Gly Gly Ile Met Leu Pro Glu Lys Ser
             25                  30                  35 caa gga aaa gta ttg caa gca aca gta gtc gct gtt gga tcg ggt tct     200
Gln Gly Lys Val Leu Gln Ala Thr Val Val Ala Val Gly Ser Gly Ser
         40                  45                  50 aaa gga aag ggt gga gag att caa cca gtt agc gtg aaa gtt gga gat     248
Lys Gly Lys Gly Gly Glu Ile Gln Pro Val Ser Val Lys Val Gly Asp
     55                  60                  65 aaa gtt ctt ctc cca gaa tat gga ggc acc aaa gta gtt cta gat gac     296
Lys Val Leu Leu Pro Glu Tyr Gly Gly Thr Lys Val Val Leu Asp Asp
 70                  75                  80                  85 aag gat tat ttc cta ttt aga gat ggt gac att ctt gga aag tac gta     344
Lys Asp Tyr Phe Leu Phe Arg Asp Gly Asp Ile Leu Gly Lys Tyr Val
                 90                  95                 100 gac tgaaataagt cactattgaa atggcatcaa catgatgctg cccattccac          397
Asp tgaagttctg aaatctttcg tcatgtaaat aatttccata tttctctttt ataataaact    457
aatgataact aatgacatcc agtgtctcca aaattgtttc cttgtactga tataaacact    517
tccaaataaa aatatgtaaa t                                              538

<210> SEQ ID NO 4
<211> LENGTH: 102
<212> TYPE: PRT
<213> ORGANISM: Homo sapiens

<400> SEQUENCE: 4
```

```
Met Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
                35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 5
<211> LENGTH: 34
<212> TYPE: DNA
<213> ORGANISM: Artificial Sequence
<220> FEATURE:
<223> OTHER INFORMATION: hDRR4 forward primer

<400> SEQUENCE: 5
cagaattcgc caccatggat ccaacggtct caac        34

<210> SEQ ID NO 6
<211> LENGTH: 30
<212> TYPE: DNA
<213> ORGANISM: Artificial Sequence
<220> FEATURE:
<223> OTHER INFORMATION: hDRR4 reverse primer

<400> SEQUENCE: 6
gtctcgagtc actgctccaa tctgcttccc        30

<210> SEQ ID NO 7
<211> LENGTH: 54
<212> TYPE: DNA
<213> ORGANISM: Homo sapiens
<220> FEATURE:
<221> NAME/KEY: CDS
<222> LOCATION: (1)..(54)
<223> OTHER INFORMATION:

<400> SEQUENCE: 7

```
gcg ttt aga aag ttt ctt cca ctc ttt gac cga gta ttg gtt gaa agg   48
Ala Phe Arg Lys Phe Leu Pro Leu Phe Asp Arg Val Leu Val Glu Arg
1               5                   10                  15 agt gct                                                            54
Ser Ala
```

<210> SEQ ID NO 8
<211> LENGTH: 18
<212> TYPE: PRT
<213> ORGANISM: Homo sapiens

<400> SEQUENCE: 8

```
Ala Phe Arg Lys Phe Leu Pro Leu Phe Asp Arg Val Leu Val Glu Arg
1               5                   10                  15

Ser Ala
```

<210> SEQ ID NO 9

-continued

```
<211> LENGTH: 2060
<212> TYPE: DNA
<213> ORGANISM: Homo sapiens
<220> FEATURE:
<221> NAME/KEY: CDS
<222> LOCATION: (220)..(1344)
<223> OTHER INFORMATION:

<400> SEQUENCE: 9
tgttcccagc actcaagcct tgccaccgcc gagccgggct tcctgggtgt ttcaggcaag      60
gaagtctagg tccctggggg gtgaccccca aggaaaaggc agcctccctg cgcacccggt     120
tgcccggagc cctctccagg gccggctggg ctggggttg  ccctggccag caggggcccg     180
ggggcgatgc cacccggtgc cgactgaggc caccgcacc atg gcc cgc tcg ctg        234
                                           Met Ala Arg Ser Leu
                                            1               5 acc tgg cgc tgc tgc ccc tgg tgc ctg acg gag gat gag aag gcc gcc       282
Thr Trp Arg Cys Cys Pro Trp Cys Leu Thr Glu Asp Glu Lys Ala Ala
                10                  15                  20 gcc cgg gtg gac cag gag atc aac agg atc ctc ttg gag cag aag aag       330
Ala Arg Val Asp Gln Glu Ile Asn Arg Ile Leu Leu Glu Gln Lys Lys
        25                  30                  35 cag gac cgc ggg gag ctg aag ctg ctg ctt ttg ggc cca ggc gag agc       378
Gln Asp Arg Gly Glu Leu Lys Leu Leu Leu Leu Gly Pro Gly Glu Ser
    40                  45                  50 ggg aag agc acc ttc atc aag cag atg cgg atc atc cac ggc gcc ggc       426
Gly Lys Ser Thr Phe Ile Lys Gln Met Arg Ile Ile His Gly Ala Gly
55                  60                  65 tac tcg gag gag gag cgc aag ggc ttc cgg ccc ctg gtc tac cag aac       474
Tyr Ser Glu Glu Glu Arg Lys Gly Phe Arg Pro Leu Val Tyr Gln Asn
70                  75                  80                  85 atc ttc gtg tcc atg cgg gcc atg atc gag gcc atg gag cgg ctg cag       522
Ile Phe Val Ser Met Arg Ala Met Ile Glu Ala Met Glu Arg Leu Gln
                90                  95                 100 att cca ttc agc agg ccc gag agc aag cac cac gct agc ctg gtc atg       570
Ile Pro Phe Ser Arg Pro Glu Ser Lys His His Ala Ser Leu Val Met
            105                 110                 115 agc cag gac ccc tat aaa gtg acc acg ttt gag aag cgc tac gct gcg       618
Ser Gln Asp Pro Tyr Lys Val Thr Thr Phe Glu Lys Arg Tyr Ala Ala
        120                 125                 130 gcc atg cag tgg ctg tgg agg gat gcc ggc atc cgg gcc tgc tat gag       666
Ala Met Gln Trp Leu Trp Arg Asp Ala Gly Ile Arg Ala Cys Tyr Glu
    135                 140                 145 cgt cgg cgg gaa ttc cac ctg ctc gat tca gcc gtg tac tac ctg tcc       714
Arg Arg Arg Glu Phe His Leu Leu Asp Ser Ala Val Tyr Tyr Leu Ser
150                 155                 160                 165 cac ctg gag cgc atc acc gag gag ggc tac gtc ccc aca gct cag gac       762
His Leu Glu Arg Ile Thr Glu Glu Gly Tyr Val Pro Thr Ala Gln Asp
                170                 175                 180 gtg ctc cgc agc cgc atg ccc acc act ggc atc aac gag tac tgc ttc       810
Val Leu Arg Ser Arg Met Pro Thr Thr Gly Ile Asn Glu Tyr Cys Phe
            185                 190                 195 tcc gtg cag aaa acc aac ctg cgg atc gtg gac gtc ggg ggc cag aag       858
Ser Val Gln Lys Thr Asn Leu Arg Ile Val Asp Val Gly Gly Gln Lys
        200                 205                 210 tca gag cgt aag aaa tgg atc cat tgt ttc gag aac gtg atc gcc ctc       906
Ser Glu Arg Lys Lys Trp Ile His Cys Phe Glu Asn Val Ile Ala Leu
    215                 220                 225 atc tac ctg gcc tca ctg agt gaa tac gac cag tgc ctg gag gag aac       954
Ile Tyr Leu Ala Ser Leu Ser Glu Tyr Asp Gln Cys Leu Glu Glu Asn
230                 235                 240                 245
```

```
aac cag gag aac cgc atg aag gag agc ctc gca ttg ttt ggg act atc      1002
Asn Gln Glu Asn Arg Met Lys Glu Ser Leu Ala Leu Phe Gly Thr Ile
                250                 255                 260 ctg gaa cta ccc tgg ttc aaa agc aca tcc gtc atc ctc ttt ctc aac      1050
Leu Glu Leu Pro Trp Phe Lys Ser Thr Ser Val Ile Leu Phe Leu Asn
            265                 270                 275 aaa acc gac atc ctg gag gag aaa atc ccc acc tcc cac ctg gct acc      1098
Lys Thr Asp Ile Leu Glu Glu Lys Ile Pro Thr Ser His Leu Ala Thr
        280                 285                 290 tat ttc ccc agt ttc cag ggc cct aag cag gat gct gag gca gcc aag      1146
Tyr Phe Pro Ser Phe Gln Gly Pro Lys Gln Asp Ala Glu Ala Ala Lys
    295                 300                 305 agg ttc atc ctg gac atg tac acg agg atg tac acc ggg tgc gtg gac      1194
Arg Phe Ile Leu Asp Met Tyr Thr Arg Met Tyr Thr Gly Cys Val Asp
310                 315                 320                 325 ggc ccc gag ggc agc aag aag ggc gca cga tcc cga cgc ctt ttc agc      1242
Gly Pro Glu Gly Ser Lys Lys Gly Ala Arg Ser Arg Arg Leu Phe Ser
                330                 335                 340 cac tac aca tgt gcc aca gac aca cag aac atc cgc aag gtc ttc aag      1290
His Tyr Thr Cys Ala Thr Asp Thr Gln Asn Ile Arg Lys Val Phe Lys
            345                 350                 355 gac gtg cgg gac tcg gtg ctc gcc cgc tac ctg gac gag atc aac ctg      1338
Asp Val Arg Asp Ser Val Leu Ala Arg Tyr Leu Asp Glu Ile Asn Leu
        360                 365                 370 ctg tga cccaggcccc acctgggca ggcggcaccg gcgggcgggt gggaggtggg        1394
Leu agtggctgca gggaccctag tgtcctggtc tatctctcca gcctcggccc acacgcaagg    1454
gagtcggggg acggcccgct gctggccgct ctcttctctg cctctcacca ggacagccgc    1514
cccccagggt actcctgccc ttgcttgact cagtttccct cctttgaaag ggaaggagca    1574
aaacggccat ttgggatgcc agggtggatg aaaaggtgaa gaaatcaggg gattgagact    1634
tgggtgggtg ggcatctctc aggagcccca tctccgggcg tgtcacctcc tgggcagggt    1694
tctgggaccc tctgtgggtg acgcacaccc tgggatgggg ctagtagagc cttcaggcgc    1754
cttcgggcgt ggactctggc gcactctagt ggacaggaga aggaacgcct tccaggaacc    1814
tgtggactag gggtgcaggg acttcccttt gcaaggggta acagaccgct ggaaaacact    1874
gtcactttca gagctcggtg gctcacagcg tgtcctgccc cggtttgcgg acgagagaaa    1934
tcgcggccca caagcatccc ccatcccttg caggctgggg gctgggcatg ctgcatctta    1994 acctttgta tttattccct caccttctgc agggctccgt gcgggctgaa attaaagatt     2054
tcttag                                                               2060

<210> SEQ ID NO 10
<211> LENGTH: 374
<212> TYPE: PRT
<213> ORGANISM: Homo sapiens

<400> SEQUENCE: 10

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60
```

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
        355                 360                 365

Asp Glu Ile Asn Leu Leu
    370

<210> SEQ ID NO 11
<211> LENGTH: 1176
<212> TYPE: DNA
<213> ORGANISM: Homo sapiens
<220> FEATURE:
<221> NAME/KEY: CDS
<222> LOCATION: (149)..(1141)
<223> OTHER INFORMATION:

<400> SEQUENCE: 11
ttaatctctt caagcctctg atttcctctc ctgtaaaaca ggggcggtaa ttaccacata      60
acaggctggt catgaaaatc agtgaacatg cagcaggtgc tcaagtcttg tttttgtttc     120 cagggggcacc agtggaggtt ttctgagc atg gat cca acc acc ccg gcc tgg       172
                                Met Asp Pro Thr Thr Pro Ala Trp -continued

```
        1               5
gga aca gaa agt aca aca gtg aat gga aat gac caa gcc ctt ctt ctg    220
Gly Thr Glu Ser Thr Thr Val Asn Gly Asn Asp Gln Ala Leu Leu Leu
 10              15                  20 ctt tgt ggc aag gag acc ctg atc ccg gtc ttc ctg atc ctt ttc att    268
Leu Cys Gly Lys Glu Thr Leu Ile Pro Val Phe Leu Ile Leu Phe Ile
 25              30                  35                  40 gcc ctg gtc ggg ctg gta gga aac ggg ttt gtg ctc tgg ctc ctg ggc    316
Ala Leu Val Gly Leu Val Gly Asn Gly Phe Val Leu Trp Leu Leu Gly
                 45                  50                  55 ttc cgc atg cgc agg aac gcc ttc tct gtc tac gtc ctc agc ctg gcc    364
Phe Arg Met Arg Arg Asn Ala Phe Ser Val Tyr Val Leu Ser Leu Ala
             60                  65                  70 ggg gcc gac ttc ctc ttc ctc tgc ttc cag att ata aat tgc ctg gtg    412
Gly Ala Asp Phe Leu Phe Leu Cys Phe Gln Ile Ile Asn Cys Leu Val
         75                  80                  85 tac ctc agt aac ttc ttc tgt tcc atc tcc atc aat ttc cct agc ttc    460
Tyr Leu Ser Asn Phe Phe Cys Ser Ile Ser Ile Asn Phe Pro Ser Phe
     90                  95                 100 ttc acc act gtg atg acc tgt gcc tac ctt gca ggc ctg agc atg ctg    508
Phe Thr Thr Val Met Thr Cys Ala Tyr Leu Ala Gly Leu Ser Met Leu
105                 110                 115                 120 agc acc gtc agc acc gag cgc tgc ctg tcc gtc ctg tgg ccc atc tgg    556
Ser Thr Val Ser Thr Glu Arg Cys Leu Ser Val Leu Trp Pro Ile Trp
                125                 130                 135 tat cgc tgc cgc cgc ccc aga cac ctg tca gcg gtc gtg tgt gtc ctg    604
Tyr Arg Cys Arg Arg Pro Arg His Leu Ser Ala Val Val Cys Val Leu
            140                 145                 150 ctc tgg gcc ctg tcc cta ctg ctg agc atc ttg gaa ggg aag ttc tgt    652
Leu Trp Ala Leu Ser Leu Leu Leu Ser Ile Leu Glu Gly Lys Phe Cys
        155                 160                 165 ggc ttc tta ttt agt gat ggt gac tct ggt tgg tgt cag aca ttt gat    700
Gly Phe Leu Phe Ser Asp Gly Asp Ser Gly Trp Cys Gln Thr Phe Asp
    170                 175                 180 ttc atc act gca gcg tgg ctg att ttt tta ttc atg gtt ctc tgt ggg    748
Phe Ile Thr Ala Ala Trp Leu Ile Phe Leu Phe Met Val Leu Cys Gly
185                 190                 195                 200 tcc agt ctg gcc ctg ctg gtc agg atc ctc tgt ggc tcc agg ggt ctg    796
Ser Ser Leu Ala Leu Leu Val Arg Ile Leu Cys Gly Ser Arg Gly Leu
                205                 210                 215 cca ctg acc agg ctg tac ctg acc atc ctg ctc aca gtg ctg gtg ttc    844
Pro Leu Thr Arg Leu Tyr Leu Thr Ile Leu Leu Thr Val Leu Val Phe
            220                 225                 230 ctc ctc tgc ggc ctg ccc ttt ggc att cag tgg ttc cta ata tta tgg    892
Leu Leu Cys Gly Leu Pro Phe Gly Ile Gln Trp Phe Leu Ile Leu Trp
        235                 240                 245 atc tgg aag gat tct gat gtc tta ttt tgt cat att cat cca gtt tca    940
Ile Trp Lys Asp Ser Asp Val Leu Phe Cys His Ile His Pro Val Ser
    250                 255                 260 gtt gtc ctg tca tct ctt aac agc agt gcc aac ccc atc att tac ttc    988
Val Val Leu Ser Ser Leu Asn Ser Ser Ala Asn Pro Ile Ile Tyr Phe
265                 270                 275                 280 ttc gtg ggc tct ttt agg aag cag tgg cgg ctg cag cag ccg atc ctc    1036
Phe Val Gly Ser Phe Arg Lys Gln Trp Arg Leu Gln Gln Pro Ile Leu
                285                 290                 295 aag ctg gct ctc cag agg gct ctg cag gac att gct gag gtg gat cac    1084
Lys Leu Ala Leu Gln Arg Ala Leu Gln Asp Ile Ala Glu Val Asp His
            300                 305                 310 agt gaa gga tgc ttc cgt cag ggc acc ccg gag atg tcg aga agc agt    1132
```

```
Ser Glu Gly Cys Phe Arg Gln Gly Thr Pro Glu Met Ser Arg Ser Ser
        315                 320                 325 ctg gtg tag agatggacag cctctacttc catcagatat atgtg               1176
Leu Val
    330

<210> SEQ ID NO 12
<211> LENGTH: 330
<212> TYPE: PRT
<213> ORGANISM: Homo sapiens

<400> SEQUENCE: 12

Met Asp Pro Thr Thr Pro Ala Trp Gly Thr Glu Ser Thr Thr Val Asn
1               5                   10                  15

Gly Asn Asp Gln Ala Leu Leu Leu Cys Gly Lys Glu Thr Leu Ile
            20                  25                  30

Pro Val Phe Leu Ile Leu Phe Ile Ala Leu Val Gly Leu Val Gly Asn
        35                  40                  45

Gly Phe Val Leu Trp Leu Leu Gly Phe Arg Met Arg Arg Asn Ala Phe
    50                  55                  60

Ser Val Tyr Val Leu Ser Leu Ala Gly Ala Asp Phe Leu Phe Leu Cys
65                  70                  75                  80

Phe Gln Ile Ile Asn Cys Leu Val Tyr Leu Ser Asn Phe Phe Cys Ser
                85                  90                  95

Ile Ser Ile Asn Phe Pro Ser Phe Phe Thr Thr Val Met Thr Cys Ala
            100                 105                 110

Tyr Leu Ala Gly Leu Ser Met Leu Ser Thr Val Ser Thr Glu Arg Cys
        115                 120                 125

Leu Ser Val Leu Trp Pro Ile Trp Tyr Arg Cys Arg Arg Pro Arg His
    130                 135                 140

Leu Ser Ala Val Val Cys Val Leu Leu Trp Ala Leu Ser Leu Leu Leu
145                 150                 155                 160

Ser Ile Leu Glu Gly Lys Phe Cys Gly Phe Leu Phe Ser Asp Gly Asp
                165                 170                 175

Ser Gly Trp Cys Gln Thr Phe Asp Phe Ile Thr Ala Ala Trp Leu Ile
            180                 185                 190

Phe Leu Phe Met Val Leu Cys Gly Ser Ser Leu Ala Leu Leu Val Arg
        195                 200                 205

Ile Leu Cys Gly Ser Arg Gly Leu Pro Leu Thr Arg Leu Tyr Leu Thr
    210                 215                 220

Ile Leu Leu Thr Val Leu Val Phe Leu Leu Cys Gly Leu Pro Phe Gly
225                 230                 235                 240

Ile Gln Trp Phe Leu Ile Leu Trp Ile Trp Lys Asp Ser Asp Val Leu
                245                 250                 255

Phe Cys His Ile His Pro Val Ser Val Val Leu Ser Ser Leu Asn Ser
            260                 265                 270

Ser Ala Asn Pro Ile Ile Tyr Phe Phe Val Gly Ser Phe Arg Lys Gln
        275                 280                 285

Trp Arg Leu Gln Gln Pro Ile Leu Lys Leu Ala Leu Gln Arg Ala Leu
    290                 295                 300

Gln Asp Ile Ala Glu Val Asp His Ser Glu Gly Cys Phe Arg Gln Gly
305                 310                 315                 320

Thr Pro Glu Met Ser Arg Ser Ser Leu Val
                325                 330
```

```
<210> SEQ ID NO 13
<211> LENGTH: 33
<212> TYPE: DNA
<213> ORGANISM: Artificial Sequence
<220> FEATURE:
<223> OTHER INFORMATION: hDRR7 forward primer

<400> SEQUENCE: 13
cgaattccgc caccatggat ccaaccaccc cgg                                33

<210> SEQ ID NO 14
<211> LENGTH: 34
<212> TYPE: DNA
<213> ORGANISM: Artificial sequence
<220> FEATURE:
<223> OTHER INFORMATION: hDRR7 reverse primer

<400> SEQUENCE: 14
gctctagagg ctgtccatct ctacaccaga ctgc                               34

<210> SEQ ID NO 15
<211> LENGTH: 21
<212> TYPE: DNA
<213> ORGANISM: Artificial Sequence
<220> FEATURE:
<223> OTHER INFORMATION: hDRR7 forward QPCR primer

<400> SEQUENCE: 15
tggaaatgac caagcccttc t                                             21

<210> SEQ ID NO 16
<211> LENGTH: 21
<212> TYPE: DNA
<213> ORGANISM: Artificial Sequence
<220> FEATURE:
<223> OTHER INFORMATION: hDRR7 reverse primer QPCR

<400> SEQUENCE: 16
gaaaaggatc aggaagaccg g                                             21

<210> SEQ ID NO 17
<211> LENGTH: 27
<212> TYPE: DNA
<213> ORGANISM: Artificial Sequence
<220> FEATURE:
<223> OTHER INFORMATION: hDRR7 FAM-probe QPCR

<400> SEQUENCE: 17
atcagggtct ccttgccaca aagcagt                                       27

<210> SEQ ID NO 18
<211> LENGTH: 18
<212> TYPE: PRT
<213> ORGANISM: Homo sapiens

<400> SEQUENCE: 18

Leu Gly Lys Ala Phe Arg Lys Phe Leu Pro Leu Phe Asp Arg Val Leu
1               5                   10                  15

Val Glu

<210> SEQ ID NO 19
<211> LENGTH: 18
<212> TYPE: PRT
<213> ORGANISM: Homo sapiens

<400> SEQUENCE: 19
```

```
Leu Gly Gln Ala Phe Arg Lys Phe Leu Pro Leu Phe Asp Arg Val Leu
1               5                   10                  15

Val Glu

<210> SEQ ID NO 20
<211> LENGTH: 16
<212> TYPE: PRT
<213> ORGANISM: Homo sapiens

<400> SEQUENCE: 20

Leu Gly Lys Ala Phe Arg Lys Phe Leu Pro Leu Phe Asp Arg Val Leu
1               5                   10                  15

<210> SEQ ID NO 21
<211> LENGTH: 16
<212> TYPE: PRT
<213> ORGANISM: Homo sapiens

<400> SEQUENCE: 21

Leu Gly Gln Ala Phe Arg Lys Phe Leu Pro Leu Phe Asp Arg Val Leu
1               5                   10                  15

<210> SEQ ID NO 22
<211> LENGTH: 17
<212> TYPE: DNA
<213> ORGANISM: Artificial Sequence
<220> FEATURE:
<223> OTHER INFORMATION: hDRR4 forward primer QPCR

<400> SEQUENCE: 22
gcgcaggaac gccttct                                                17

<210> SEQ ID NO 23
<211> LENGTH: 17
<212> TYPE: DNA
<213> ORGANISM: Artificial Sequence
<220> FEATURE:
<223> OTHER INFORMATION: hDRR4 reverse primer QPCR

<400> SEQUENCE: 23
cggccgctga ggaagag                                                17

<210> SEQ ID NO 24
<211> LENGTH: 22
<212> TYPE: DNA
<213> ORGANISM: Artificial Sequence
<220> FEATURE:
<223> OTHER INFORMATION: hDRR4 FAM-probe QPCR

<400> SEQUENCE: 24
tcctcaactt ggccgcagca ga                                          22
```

EPF DERIVED PEPTIDES AND THERAPEUTIC COMPOSITIONS

CROSS REFERENCE TO RELATED APPLICATIONS

This application is a continuation of U.S. patent application Ser. No. 10/481,161, filed Dec. 17, 2003 now abandoned, which is the U.S. National Stage of International Application No. PCT/EP02/07263, filed Jun. 26, 2002, and which claims the benefit of European patent application 01202474.1, filed Jun. 27, 2001; each of which is hereby incorporated by reference.

This invention relates to the field of assays for compounds that interact with the receptor for Early Pregnancy Factor (EPF), also known as Chaperonin 10 and EPF-related peptides as well as the therapeutic use thereof.

BACKGROUND OF THE INVENTION

EPF and the mitochondrial chaperonin 10 have identical amino acid sequences (SEQ ID NO:4) although they may be encoded by different genes (Summers et al., 1998) and have very different physiological functions. Moreover, EPF is a secreted peptide, whereas chaperonin 10 is found in the intracellular vesicles along the secretory pathway.

Chaperonin 10 belongs to the family of heat shock proteins. In the mitochondria it forms a chaperonin complex with heat shock protein 60 which is important for mitochondrial protein folding and function. Upon ischemia, upregulation of these two proteins is able to protect brain tissue as well as cardiac myocytes (Lau et al., 1997) against ischemia/reperfusion injury (Hickey et al., 2000).

Up until now, EPF is mainly known as an important factor in embryonic development, in the pre-implementation stage as well as in the peri-implantation stage (Athanasas-Platsis et al., 2000). Its importance in these two phases is based on its growth regulatory and immunomodulatory properties. These actions of EPF are also apparent as it is produced by proliferating primary and neoplastic cells, where it functions as an autocrine growth factor both in vitro and in vivo (Morton, 1998).

The presence of EPF has been repeatedly confirmed as indispensable to successful pregnancy. Recently, Cheng S J et al. (Am. J. Reprod. Immunol. 2000 October; 44(4):211-3) demonstrated that the EPF level declined rapidly after surgical abortion and as such suggests that monitoring the EPF activity is a useful index for embryonic care and development of normal pregnancy. Accordingly suppression of EPF activity could have a contraceptive purpose, whilst enhancing EPF activity may prevent foetal loss.

EPF is already secreted into maternal serum within 6-12 hours after fertilisation, and EPF or EPF-derived or -related peptides could therefore be a useful early marker for diagnosing pregnancy. Such diagnostic would be useful in human medicine but also for veterinary applications. Currently used EPF assays (e.g. rosette test) are cumbersome and unreliable. Moreover, they do not distinguish between various forms of EPF. Tests based on antibodies specific for (poly)peptides with EPF activity or assays that distinguish the various forms of bioactive EPF (e.g. based on chromatography and/or mass spectroscopy) may therefore offer significant advantages. EPF activity has been repeatedly confirmed as indispensable to successful pregnancy. Recently, Cheng S J et al. (Am. J. Reprod. Immunol. 2000 October; 44(4):211-3) demonstrated that the EPF level declined rapidly after surgical abortion and as such suggests that monitoring the EPF activity is a useful index for embryonic well-being and development of normal pregnancy. Accordingly, suppression of EPF activity could have a contraceptive purpose, whilst enhancing physiological or correcting abnormal EPF activity may prevent foetal loss.

It has been observed that pregnancy has a positive influence on the development of multiple sclerosis by decreasing the rate of relapses during pregnancy (Confavreux et al., 1998). As pointed out by Morton (1998), EPF is 'considered to be one of the major factors involved in the modification of multiple sclerosis observed during pregnancy'. The positive effect of the immunosuppressive action of EPF during pregnancy could also be observed for another auto-immune disease, rheumatoid arthritis (Davis and Maslow, 1992).

The potential activities of EPF and chaperonin 10 in human systems make the peptides a target for studies aimed at identifying compounds that enhance or diminish the biological effects of the peptides. However, while binding sites for EPF and chaperonin 10 were shown to exist, no receptor for these peptides was identified. The lack of a known receptor has hampered the design of assays and impeded efforts to discover and study compounds that mimic or alter the biological effects of EPF or chaperonin 10.

The present invention solves this problem in the art as reverse pharmacology has led to the identification of the human Dorsal Root Receptors (hDRRs) as receptor proteins for EPF or chaperonin 10. With this finding the present inventors further substantiate the immunomodulatory properties of EPF as hDRR receptors are shown to be expressed in lymph nodes and chromosomal mapping of the hDRRs to chromosome 11p15 linked them to a number of lymphoblastic leukemias. It further provides assays to identify compounds that mimic or alter the biological effects of EPF or chaperonin 10, as well as the pharmacological use thereof.

hDRRs belongs to the family of G protein coupled receptors (GPCRs) which share a common structural organization characterized by an extracellular N-terminal end, seven hydrophobic alpha helices putatively constituting transmembrane domains and an intracellular C-terminal domain. GPCRs bind a variety of ligands that trigger intracellular signals through the activation of transducing G proteins (Caron et al., Rec. Prog. Horm. Res. 48:277-290 (1993); Freedman et al., Rec. Prog. Horm. Res. 51:319-353 (1996)).

Recent reviews (Stadel et al., 1997; Wilson et al., 1998) count the number of GPCRs being used as a target for commercially useful drugs to 25, this constitutes 18% of the 140 characterized cloned human GPCRs. Extrapolation from fully sequenced genomes (yeast, *C. elegans*) to the expected 30.000 human genes leads to the expectation that 5000 human GPCRs will be found in the course of the next 3 years. In analogy to the current numbers, 150 of these novel orphan GPCRs should develop into a target of a commercially interesting drug during the next decade. This calculation does not take into account that additional characterized GPCRs are currently the basis of compounds in development.

In general, it is fair to say that reverse pharmacology on orphan GPCRs will deliver novel approaches for the treatment of various diseases, which will outcompete current strategies or enable treatment of conditions that cannot be treated by current means. This has been recognized by the pharmaceutical industry as is documented by recent publications on orphan GPCR ligand identification (orphanin FQ (Reinscheid et al, 1995.), orexin (Sakurai et al, 1998), pro-lactin-releasing peptide (Hinuma et al.), apelin (Tatemoto et al., 1998).

The nucleic acid and polypeptide sequences of the human Dorsal Root Receptors 1-6 were described in PCT application WO 99/32519 A1 published Jul. 1, 1999. Based on their homology to the rat Dorsal Root Receptor, this document describes the hDRR receptors as being involved in transmission, modulation and sensation of pain, including the use thereof in assays for the identification of new agents for anesthesia and analgesia. In this PCT application the Dorsal Root Ganglia localization has been confirmed for hDRR5 in fetal dorsal root ganglia. However, for none of the human adult tissues examined thus far, including dorsal root ganglia, a hDRR specific hybridization signal could be detected. In addition for none of the disclosed hDRR receptors in this application (WO 99/32519 A1) a natural ligand could be identified. The characterization of hDRR4 as an angiotensin receptor in aforesaid application (WO 99/32519-A1), based upon the stimulation of this receptor with angiotensin II and III, could not be confirmed by the present inventors.

For another human Dorsal Root Receptor, hDRR7, the nucleic acid and polypeptide sequences were described in PCT applications WO 01/16159-A1 published Mar. 8, 2001 and in WO 01/19983-A1 published Mar. 22, 2001. In neither of these documents a ligand for the hDRR7 receptor has been identified. In PCT application WO 01/16159-A1 the hDRR7 receptor is referred to as TheAnt disclosing a large number of conditions associated with said polypeptide. However, no substantive evidence is provided to link this receptor to any of the enlisted disease states. In PCT application WO 01/19983 the hDRR7 receptor is generally described as a GPCR with low sequence similarity to the somatostatin 3 receptor.

Therefore, no assay employing competition with a natural ligand for hDRRs, or employing a comparison to the interaction of the hDRRs with a natural ligand has been described. The latter is essential to use the hDRRs as pharmacological tools to explore receptor function and relationship to disease states. The present invention solves this problem in the art and provides assays that employ the interaction of hDRRs and EPF or EPF-related peptides, to determine whether a candidate compound is a ligand, agonist or antagonist of hDRRs.

Only recently, Lembo et al. (Nature Neuroscience 5, 201-209 (2002)) demonstrated that the hDRR 4 receptor, also known as Sensory Neuron—Specific G protein coupled—Receptor 4 (SNSR4) or Mas Related Gene Receptor 1 (hMrgX1), are potently activated by gene products of the opioid peptide precursor proenkephalin A. In particular BAM22 and BAM22 fragments, known to be involved in the control of nociception, were shown to activate the hDRR in a FLIPR based calcium assay.

In the present invention EPF and EPF-related peptides were shown to activate both the hDRR4 and hDRR7 receptors. Further, hDRR4 was shown to be predominantly expressed in dorsal root and trigeminal ganglia (Lembo et al., Nature Neuroscience 5, 201-209 (2002)), whilst for hDRR7 it has now been demonstrated that this receptor is predominantly expressed in lymph nodes. This receptor specific expression pattern suggests a different functionality in response to ligand activation.

It would accordingly be beneficial if one could design receptor-specific compounds useful in treating receptor related disorders. The identification of EPF and EPF-related peptides as ligands for hDRR4 and hDRR7, now provides a basis for the development of in vitro screening methods to identify compounds capable of modulating a hDRR involvement in the transmission, modulation and sensation of pain. Furthermore, they are useful as anticonceptives, in anesthesia and analgesia and in identifying compounds capable of modulating hDRR mediated disorders such as rheumatoid arthritis, multiple sclerosis or other conditions where immunosuppressive actions are desired like Inflammatory Bowel Disease (IBD) or to prevent transplant rejection.

These and other aspects of the invention are described herein in more detail.

SUMMARY OF THE INVENTION

The present invention provides assays for the study of the interaction of EPF or EPF-related peptides, with the hDRR receptors. The assays are useful to identify whether a test compound can bind to the hDRRs under conditions in which EPF or EPF-related peptides, can bind to the receptor. The assays are also useful to determine whether the test compound is an agonist or antagonist of hDRRs. The above assays can be performed in a variety of formats including competitive, non-competitive and comparative assays in which the interaction of EPF or related peptides with hDRRs is assessed as a positive or negative control or compared to the results obtained with the test compound.

In another aspect the present invention relates to the isolated and purified polypeptide and polynucleotide molecules encoding the hDRR binding fragment of EPF having the amino acid sequence (AFRKFLPLFDRVLVERSA (SEQ ID NO:8)) as well as the diagnostic and therapeutic use thereof.

Accordingly, the present invention relates to the isolated and purified polypeptides and polynucleotide molecules encoding EPF-related peptides capable of binding and activating the hDRR receptors having the amino acid sequences ((LGKAFRKFLPLFDRVLVE (SEQ ID NO:18)), ((LGQAFRKFLPLFDRVLVE (SEQ ID NO:19)), ((LGKAFRKFLPLFDRVL (SEQ ID NO:20)) and ((LGQAFRKFLPLFDRVL (SEQ ID NO:21)) as well as the therapeutic and diagnostic use thereof.

In a further embodiment the present invention relates to pharmaceutical compositions comprising compounds identified in the assays provided by the invention, and the therapeutic use thereof as anticonceptives as well as in relation to methods of treatment of certain diseases, including but not limited to; cancers like transitional cell carcinoma, liposarcoma, adenocarcinoma, diffuse large B-cell lymphoma, lymphocytic leukemia, lymphoblastic leukemia, myeloblastic leukemia, myelomonocytic leukemia, osteosarcoma; refractory anemia when said compound; for the treatment of autoimmune diseases like rheumatoid arthritis, multiple sclerosis or other conditions where immunosuppressive actions are desired like Inflammatory Bowel Disease (IBD) or to prevent transplant rejection.

In a further aspect the present invention provides a method for isolating hDRR from a cellular fraction containing the same, comprising contacting the cellular fraction with EPF or a hDRR binding fragment thereof immobilized to a solute substrate and eluting hDRR therefrom.

BRIEF DESCRIPTION OF THE DRAWING

FIG. 1A—The nucleotide coding sequence of hDRR4 (SEQ ID NO: 1) is shown. (start and stop codons in bold)

FIG. 1B—The amino acid sequence of hDRR4 (SEQ ID NO: 2) is shown.

DETAILED DESCRIPTION

Figure 2:
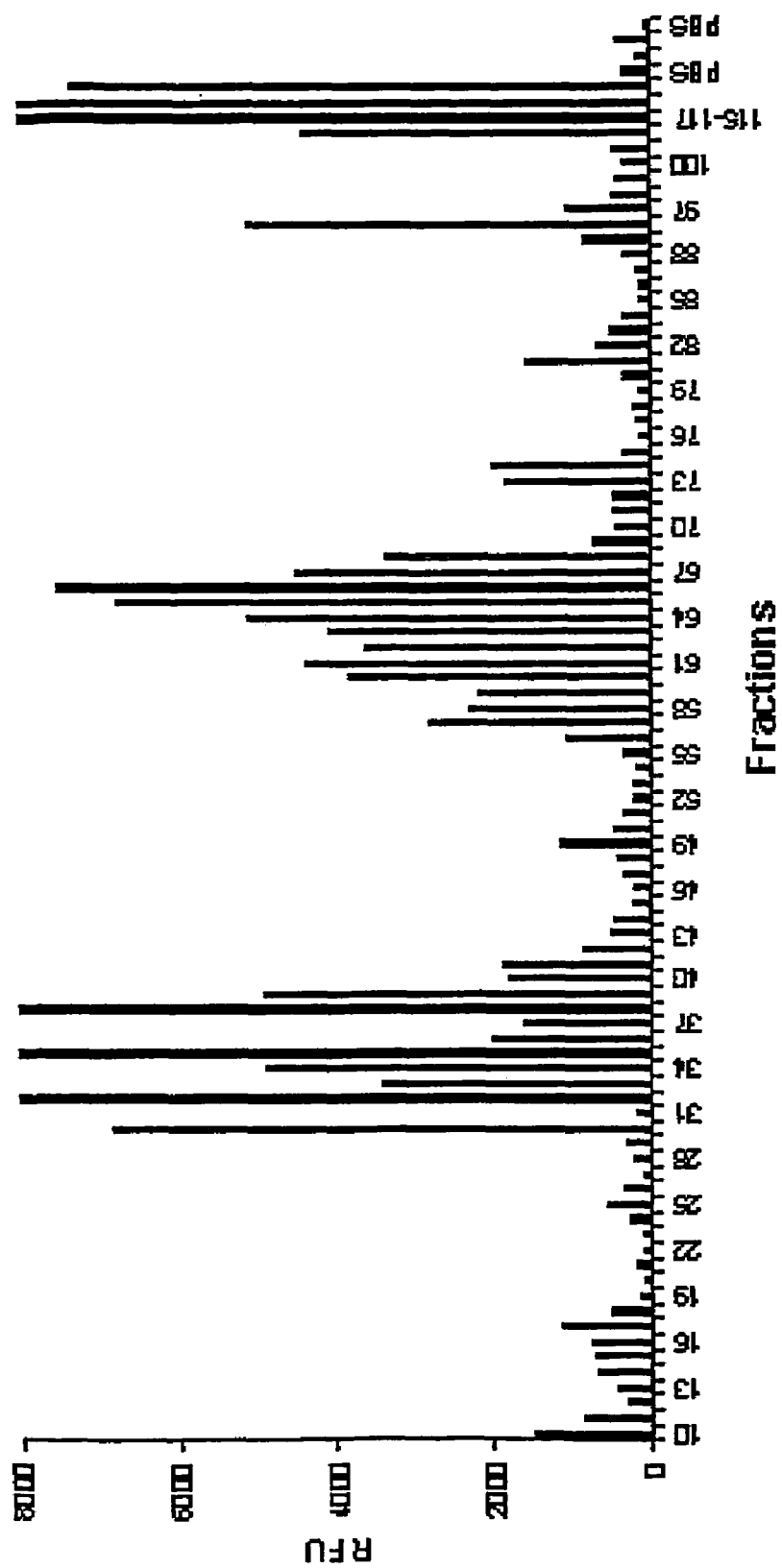
FIG. 2—Activation of orphan GPCR hDRR4 by porcine hypothalamus extract C18 fractions after transient co-transfection with Gα16-pcDNA into Hek293. Relative fluorescence units (RFU) were determined by loading the cells with Fluo-4 (Molecular Probes, Eugene, Oreg., U.S.A.) and assaying the cells for $Ca^{2+}$ transients in the FLIPR instrument (Molecular Devices, Sunnyvale, Calif., U.S.A.)

The present invention provides assays that make use of the interaction of EPF or an EPF-related peptide, with a hDRR receptor. EPF, also known as Chaperonin 10 and EPF-related peptides are high affinity ligands of hDRRs that activate the receptor when bound thereto and lead to an activation of phospholipase C which hydrolyzes inositol lipids in membranes to release inositol trisphosphate, that in turn mobilizes calcium within a cell. The assays provide methods to identify compounds that are ligands of hDRRs or are agonists or antagonists of hDRR receptors and their use in treatment of patients.

As used herein, "EPF or EPF-related peptides" refers to the early pregnancy factor, also known as chaperonin 10, having the amino acid sequence SEQ ID NO: 4 or EPF-related peptides wherein said related peptides are derived from the aforementioned sequence by way of substitution, deletion and/or addition of one or several amino acids of the amino acid sequence encoding EPF and wherein said EPF-related peptides are capable of binding to the hDRR4 receptor protein according to the invention. In a preferred embodiment said EPF-related peptides comprise the hDRR binding region encoded by SEQ ID NO:8. In a more preferred embodiment said EPF-related peptide consists of the hDRR binding region encoded by SEQ ID NO:8. In a further embodiment the EPF-related peptides comprise an amino acid sequence selected from the group consisting of ((LGKAFRKFLPLFDRVLVE (SEQ ID NO:18)), ((LGQAFRKFLPLFDRVLVE (SEQ ID NO:19)), ((LGKAFRKFLPLFDRVL (SEQ ID NO:20)) and ((LGQAFRKFLPLFDRVL (SEQ ID NO:21)). In another aspect of the invention the EPF-related peptides consist of peptides having an amino acid sequence being selected from the group consisting of (SEQ ID NO:18), (SEQ ID NO:19), (SEQ ID NO:20) and (SEQ ID NO:21).

In a specific embodiment, the hDRR receptor polypeptide in an assay according to the invention is either the hDRR4 receptor protein, comprising the amino acid sequence SEQ ID NO:2 or fragments thereof, or the hDRR7 receptor protein, comprising the amino acid sequence SEQ ID NO:12 or fragments thereof.

The term "fragments thereof" describes a piece, or sub-region of protein molecule whose sequence is disclosed herein, such that said fragment comprises 5 or more amino acids that are contiguous in the parent protein. The term "fragments thereof" is intended to include "functional fragments" wherein the isolated fragment, piece or sub-region comprises a functionally distinct region such as an active site, a binding site or a phosphorylation site of the receptor protein. Functional fragments may be produced by cloning technology, or as the natural products of alternative splicing techniques.

The term "derived from" describes a piece or sub-region of a protein molecule whose sequence is disclosed herein, such that said piece or sub-region has a high degree of sequence relatedness to the parent sequence. Said relatedness may be quantified by determining the degree of sequence identity to the parent sequence wherein a high degree of sequence relatedness refers to an isolated peptide or polypeptide having at least 70, 80, 90, 95 or 99% identity to the parent sequence as determined using local alignment.

Methods for comparing the identity and similarity of two or more sequences are well known in the art. Thus for instance, programs available in the Winconsin Sequence Analysis Package, version 9.1 (Devreux J. et al, Nucleic Acid Res., 12, 387-395, 1984), for example the programs BESTFIT and GAP, may be used to determine the % identity between two polynucleotides and the % identity and the % similarity between two peptide or polypeptide sequences. BESTFIT uses the "local homology" algorithm of Smith and Waterman (J. Mol. Biol., 147, 195-197, 1981) and finds the best single region of similarity between two sequences. BESTFIT is more suited to compare two polynucleotide or two peptide or polypeptide sequences that are dissimilar in length, the program assuming that the shorter sequence represents a portion of the longer. In comparison, GAP aligns two sequences, finding a "maximum similarity", according to the algorithm of Needleman and Wunsch (J. Mol. Biol., 48, 443-453, 1970). GAP is more suited to compare sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned. Other programs for determining identity and/or similarity between sequences are also known in the art, for instance the BLAST family of programs (Altschul S F et al, Nucleic Acids Res., 25:3389-3402, 1997).

As used herein, a "compound" is an organic or inorganic assembly of atoms of any size, and includes small molecules (less than about 2500 Daltons) or larger molecules, e.g. peptides, polypeptides, whole proteins and polynucleotides.

As used herein, a "test" compound is a compound used in a test to assess whether said test compound might be a ligand of a hDRR receptor polypeptide. A test compound may also be an agonist or antagonist of the hDRR receptor. Whether or not the test compound is an actual ligand, agonist or antagonist of a hDRR polypeptide is determined in an assay according to the invention.

As used herein, a "ligand" is a compound capable of binding to an hDRR receptor, where upon binding to the receptor a possible change in conformation of the ligand-receptor complex results in the transduction of the biological response through a second messenger. Said ligand can either be an agonist or an antagonist of the receptor.

As used herein, an "agonist" is a compound that interacts with and activates a polypeptide of the hDRR receptor. An activated hDRR receptor polypeptide induces a change in a biochemical pathway linked to the receptor, e.g. can stimulate the cleavage of GTP by a G protein, activate the adenylate cyclase pathway or activate the phospholipase C pathway.

As used herein, an "antagonist" is a compound that interacts with and inhibits or prevents the activation of a polypeptide of the hDRR receptor.

Polynucleotides

Accordingly, in a first embodiment the present invention relates to the use of an isolated and purified nucleic acid molecule which encodes hDRR or a fragment thereof, wherein said nucleic acid molecule is either RNA, DNA, cDNA or genomic DNA, in an assay that makes use of the interaction of EPF and the related peptides with the hDRR receptor.

In a second embodiment the present invention relates to the use of an isolated and purified nucleic acid molecule encoding EPF or related peptides, wherein said nucleic acid molecule is either RNA, DNA, cDNA or genomic DNA, in an assay that makes use of the interaction of EPF and the related peptides with the hDRR receptor.

As used herein, "isolated" refers to the fact that the polynucleotides, proteins and polypeptides, or respective fragments thereof in question, have been removed from their in vivo environment so that they can be manipulated by the skilled artisan, such as but not limited to sequencing, restriction digestion, site-directed mutagenesis, and subcloning into expression vectors for a nucleic acid fragment as well as obtaining the protein or protein fragments in quantities that afford the opportunity to generate polyclonal antibodies, monoclonal antibodies, amino acid sequencing, and peptide digestion. Therefore, the nucleic acids claimed herein can be present in whole cells or in cell lysates or in a partially, substantially or wholy purified form.

A polynucleotide is considered "purified" when it is purified away from environmental contaminants. Thus a polynucleotide isolated from cells is considered to be substantially purified when purified from cellular components by standard methods while a chemically synthesized nucleic acid sequence is considered to be substantially purified when purified from its chemical precursors. A "substantially pure" protein or nucleic acid will typically comprise at least 85% of a sample with greater percentages being preferred. One method for determining the purity of a protein or nucleic acid molecule, is by electrophoresing a preparation in a matrix such as polyacrylamide or agarose. Purity is evidenced by the appearance of a single band after staining. Other methods for assessing purity include chromatography, mass spectrometry and analytical centrifugation.

The term "fragments thereof" describes a piece, or sub-region of a nucleic acid molecule whose sequence is disclosed herein, such that said fragment comprises 15 or more nucleotides that are contiguous in the parent nucleic acid molecule. The term "fragments thereof" is intended to include "functional fragments" wherein the isolated fragment, piece or sub-region comprises a functionally distinct region such as an active site, a binding site or a phosphorylation site of a receptor. Functional fragments may be produced by cloning technology, or as the natural products of alternative splicing techniques.

In particular, the present invention encompasses the use in an assay according to the invention, of an isolated and purified nucleic acid molecule encoding hDRR4 or a fragment thereof, comprising a member selected from a group consisting of:
(a) a nucleic acid molecule encoding hDRR4 comprising the amino acid sequence of SEQ ID NO:2;
(b) a nucleic acid molecule comprising the nucleotide sequence of SEQ ID NO:1, encoding hDRR4;
(c) a nucleic acid molecule which is complementary to the polynucleotide of (a) or (b);
(d) a nucleic acid molecule comprising at least 15 sequential bases of the polynucleotide of (a), (b) or (c);
(e) a nucleic acid molecule that hybridizes under stringent conditions to the polynucleotide molecule of (a), (b) or (c); or
(f) a nucleic acid molecule encoding a hDRR4 protein comprising a nucleotide sequence which is degenerated as a result of the genetic code to a nucleotide sequence of a polynucleotide of any of (a) to (e).

In a more preferred embodiment of the present invention the hDRR4 encoding nucleic acid molecule consists of SEQ ID NO:1.

Accordingly, the present invention encompasses the use in an assay according to the invention, of an isolated and purified nucleic acid molecule encoding hDRR7 or a fragment thereof, comprising a member selected from a group consisting of:
(a) a nucleic acid molecule encoding hDRR7 comprising the amino acid sequence of SEQ ID NO:12;
(b) a nucleic acid molecule comprising the nucleotide sequence of SEQ ID NO:11, encoding hDRR7;
(c) a nucleic acid molecule which is complementary to the polynucleotide of (a) or (b);
(d) a nucleic acid molecule comprising at least 15 sequential bases of the polynucleotide of (a), (b) or (c);
(e) a nucleic acid molecule that hybridizes under stringent conditions to the polynucleotide molecule of (a), (b) or (c); or
(f) a nucleic acid molecule encoding a hDRR7 protein comprising a nucleotide sequence which is degenerated as a result of the genetic code to a nucleotide sequence of a polynucleotide of any of (a) to (e).

In a more preferred embodiment of the present invention the hDRR7 encoding nucleic acid molecule consists of SEQ ID NO: 11.

In a further embodiment the present invention relates to the use in an assay according to the invention, of an isolated and purified nucleic acid molecule encoding EPF or EPF-related peptides, comprising a member selected from a group consisting of:
(a) a nucleic acid molecule encoding EPF comprising the amino acid sequence of SEQ ID NO:4;
(b) a nucleic acid molecule which is complementary to the polynucleotide of (a);
(c) a nucleic acid molecule comprising at least 15 sequential bases of the polynucleotide of (a) or (b);
(d) a nucleic acid molecule that hybridizes under stringent conditions to the polynucleotide molecule of (a) or (b);
(e) a nucleic acid molecule encoding a EPF-related peptide that has 70, 80, 90, 95 or 99% sequence identity to the amino acid sequence encoded by the polynucleotide molecule of (a) or (b);

(f) a nucleic acid molecule encoding a EPF polypeptide comprising a nucleotide sequence which is degenerated as a result of the genetic code to a nucleotide sequence of a polynucleotide of any of (a) to (d).

In a more preferred embodiment of the present invention the EPF encoding nucleic acid molecule consists of SEQ ID NO: 3 and the EPF-related peptide consists of a polypeptide having an amino acid sequence selected from the group consisting of SEQ ID NO:18, SEQ ID NO:19, SEQ ID NO:20 and SEQ ID NO:21, or of the hDRR4 binding fragment encoded by SEQ ID NO:8.

Those skilled in the art will recognize that owing to the degeneracy of the genetic code, numerous "silent" substitutions of nucleotide base pairs could be introduced into the sequence identified as SEQ ID NO:1, SEQ ID NO:11 or SEQ ID NO:3 without altering the identity of the encoded amino acid(s) or protein products. All such substitutions are intended to be within the scope of the invention.

The terms "complementary" or "complementarity" as used herein refer to the capacity of purine and pyrimidine nucleotides to associate through hydrogen bonding to form double-stranded nucleic acid molecules. The following base pairs are related by complementarity: guanine and cytosine; adenine and thymine; and adenine and uracil. As used herein "complementary" means that the aforementioned relationship applies to substantially all base pairs comprising two single-stranded nucleic acid molecules over the entire length of said molecules. "Partially complementary" refers to the aforementioned relationship in which one of the two single-stranded nucleic acid molecules is shorter in length than the other such that a portion of one of the molecules remains single-stranded.

The term "hybridization" as used herein refers to a process in which a single-stranded nucleic acid molecule joints with a complementary strand through nucleotide base pairing.

The term "stringency" refers to hybridization conditions. High stringency conditions disfavor non-homologous base pairing. Low stringency conditions have the opposite effect. Stringency may be altered, for example, by temperature and salt concentration. "Stringent conditions" refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. Further suitable hybridization conditions are described in the examples.

The nucleic acid sequences encoding hDRRs are preferentially expressed in dorsal root ganglia (PCT publication WO 99/32519-A1) and these ganglia may serve as a source for the isolation of nucleic acids coding for the receptor. Other cells and cell lines may also be suitable for use to isolate hDRR nucleic acids. Selection of suitable cells may be done by screening for hDRR activity in cell extracts or in whole cell assays, described herein. Cells that possess Dorsal Root Receptor activity in any one of these assays may be suitable for the isolation of hDRR nucleic acids.

Any of a variety of procedures known in the art may be used to molecularly clone hDRR nucleic acids. In one method, mRNA is isolated, and first strand cDNA synthesis is carried out. A second round of DNA synthesis can be carried out for the production of the second strand. Subsequently by the specific PCR amplification of hDRR DNA fragments through the design of degenerate oligonucleotide primers from the amino acid sequence of the purified hDRR protein or through DNA synthesis using sequence specific primers derived from the genomic DNA sequence, an isolated cDNA can be obtained.

A preferred set of primers consists of the hDRR4 forward primer (CAGAATTCGCCACCATGGATCCAACG-GTCTCAAC) (Seq ID NO:5) or a fragment thereof consisting of nucleotides 15 to 34 of SEQ ID NO:5, the hDRR4 reverse primer (GTCTCGAGTCACTGCTCCAATCTGCT-TCCC) (Seq ID NO:6) or a fragment thereof consisting of nucleotides 9 to 30 of SEQ ID NO:6, the hDRR7 forward primer (CGAATTCCGCCACCATGGATCCAACCAC-CCCGG) (SEQ ID NO:13) and the hDRR7 reverse primer (GCTCTAGAGGCTGTCCATCTCTACACCAGACTGC) (SEQ ID NO:14).

If desired the double-stranded cDNA can be cloned into any suitable vector, for example, a plasmid, thereby forming a cDNA libary. Another method is to screen a cDNA library constructed in a bacteriophage or plasmid shuttle vector with a labeled oligonucleotide probe targeted to any suitable region of SEQ ID NO: 1 or SEQ ID NO:11. See e.g. *PCR Protocols: A Guide to Method and Application*, Ed. M. Innis et al., Academic Press (1990).

Methods for constructing cDNA libraries in a suitable vector such as a plasmid or phage for propagation in prokaryotic or eukaryotic cells are well known to those skilled in the art [See e.g. Maniatis et al. Supra]. Suitable cloning vectors are well known and are widely available.

It is readily apparent to those skilled in the art that other types of libraries, as well as libraries constructed from other cells or cell types, may be useful for isolating the nucleic acid sequences according to the invention. Other types of libraries include, but are not limited to, cDNA libraries derived from other cells, from organisms other than human and mouse, and genomic DNA libraries that include YAC (yeast artificial chromosome) and cosmid libraries. Construction of genomic DNA libraries can be performed by standard techniques well known in the art. Well known genomic DNA library construction techniques can be found in T. Maniatis et al. *Molecular Cloning: A Laboratory Manual,* 2d Ed. Chap. 14 (1989).

The skilled artisan will appreciate that, in many cases, an isolated cDNA sequence will be incomplete, in that the region coding for the polypeptide is short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during the $1^{st}$ strand cDNA synthesis.

There are several methods available and well known to those skilled in the art to obtain full-length cDNAs, or extend short cDNAs, for example those based on the method of Rapid Amplification of cDNA ends (RACE) (Frohman et al., 1988, PNAS USA 85, 8998-9002), or recent modifications of this technique.

Polypeptides

The present invention also relates to the use of hDRR receptor proteins or fragments thereof in an assay that makes use of the interaction of EPF and the related peptides with the hDRR receptor, wherein said polypeptide is encoded by an isolated and purified nucleic acid molecule according to the invention.

In a further aspect of the invention, the hDRR receptor protein is the hDRR4 receptor selected from the group consisting of;
i) an isolated and purified protein which encodes hDRR4 having the amino acid sequence of SEQ ID NO:2 or a fragment thereof;

ii) cells expressing on the surface thereof the receptor protein having the amino acid sequence of SEQ ID NO:2 or a fragment thereof; or iii) membrane preparations of cells expressing on the surface thereof the polypeptide receptor having the amino acid sequence of SEQ ID NO:2 or a fragment thereof.

In a preferred embodiment the hDRR4 receptor protein comprises the amino acid sequence of SEQ ID NO:2 or fragments thereof. In a more preferred embodiment the hDRR4 receptor protein consists of the amino acid sequence of SEQ ID NO:2 or fragments thereof.

In a further aspect of the invention, the hDRR receptor protein is the hDRR7 receptor selected from the group consisting of;

i) an isolated and purified protein which encodes hDRR7 having the amino acid sequence of SEQ ID NO:12 or a fragment thereof;

ii) cells expressing on the surface thereof the receptor protein having the amino acid sequence of SEQ ID NO:12 or a fragment thereof; or iii) membrane preparations of cells expressing on the surface thereof the polypeptide receptor having the amino acid sequence of SEQ ID NO:12 or a fragment thereof.

In a preferred embodiment the hDRR7 receptor protein comprises the amino acid sequence of SEQ ID NO:12 or fragments thereof. In a more preferred embodiment the hDRR7 receptor protein consists of the amino acid sequence of SEQ ID NO:12 or fragments thereof.

The term "fragments thereof" describes a piece, or sub-region of protein molecule whose sequence is disclosed herein, such that said fragment comprises 5 or more amino acids that are contiguous in the parent protein. The term "fragments thereof" is intended to include "functional fragments" wherein the isolated fragment, piece or sub-region comprises a functionally distinct region such as an active site, a binding site or a phosphorylation site of the receptor protein. Functional fragments may be produced by cloning technology, or as the natural products of alternative splicing techniques.

In a further aspect, the present invention relates to the use of EPF and the related peptides in an assay according to the invention. In a preferred embodiment the EPF or EPF-related peptides are selected from the group consisting of;

i) an isolated polypeptide encoding EPF, comprising the amino acid sequence SEQ ID NO:4;

ii) an isolated polypeptide derived from EPF and capable of binding to hDRR4;

iii) an isolated polypeptide encoding an EPF-related peptide comprising an amino acid selected from the group consisting of SEQ ID NO:18, SEQ ID NO:19, SEQ ID NO:20 and SEQ ID NO:21; or iv) an isolated polypeptide comprising the hDRR4 binding fragment encoded by amino acid sequence SEQ ID NO:8.

In a more preferred embodiment of the present invention, EPF consists of the amino acid sequence encoded by SEQ ID NO: 4 and an EPF-related peptide consists of an amino acide sequence selected from the group consisting of SEQ ID NO:18, SEQ ID NO:19, SEQ ID NO:20 and SEQ ID NO:21, or of the hDRR4 binding fragment encoded by SEQ ID NO:8.

The receptor protein and the peptides according to the invention includes all possible conservative amino acid changes, wherein "conservative amino acid changes" refers to a replacement of one or more amino acid residue(s) in a parent receptor protein or peptide without affecting the biological activity of the parent molecule based on the art recognized substitutability of certain amino acids (See e.g. M. Dayhoff, *In Atlas of Protein Sequence and Structure*, Vol. 5, Supp. 3, pgs 345-352, 1978).

Those skilled in the art will recognize that the polypeptides according to the invention, i.e. the hDRR4 receptor protein, the hDRR7 receptor protein and EPF or EPF-related peptides, could be obtained by a plurality of recombinant DNA techniques including, for example, hybridization, polymerase chain reaction (PCR) amplification, or de novo DNA synthesis (See e.g., T. Maniatis et al. *Molecular Cloning: A Laboratory Manual*, 2d Ed. Chap. 14 (1989)).

The peptides and derivatives of the present invention can be readily prepared according to well-established, standard liquid or, preferably, solid-phase peptide synthesis methods, general descriptions of which are broadly available, or they may be prepared in solution, by the liquid phase method or by any combination of solid-phase, liquid phase and solution chemistry.

As an example, the polypeptides of the present invention can be synthesized by employing the N-a-9-fluorenylmethyloxycarbonyl or Fmoc solid phase peptide synthesis chemistry using a RaininSymphony Multiplex Peptide Synthesizer.

The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperidine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HHTU) in DMF; (5) allowing the solution to mix for 45 minutes; and (6) washing the peptide-resin three times for 30 seconds of DMF.

This cycle can be repeated as necessary with the appropriate amino acids in sequence to produce the desired peptide. Exceptions to this cycle are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. In the first coupling step in peptide synthesis, the resin can be allowed to swell to effect more efficient coupling by increasing the time of mixing in the initial DMF washes to three 15-minute washes rather than three 30 second washes.

After synthesis, the peptide can be cleaved from the resin as follows: (1) washing the peptide-resin three times for 30 seconds with DMF; (2) removing the Fmoc protective group on the amino terminus by washing two times for 15 minutes in 20% piperidine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% trisopropysilane with the peptide-resin for two hours, then filtering the peptide in the cleavage cocktail away from the resin, and precipitating the peptide out of solution by addition of two volumes of ethyl ether.

To isolate the peptide, the ether-peptide solution can be allowed to sit at −20° C. for 20 minutes, then centrifuged at 6,000×G for 5 minutes to pellet the peptide. The peptide can be washed with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

Purified biologically active hDRR proteins may have several different physical forms. The polypeptides according to the invention may exist as a full-length nascent or unprocessed polypeptides, or as partially processed polypeptides or combinations of processed polypeptides. The full-length nascent polypeptide may be post-translationally modified, amongst other, by specific proteolytic cleavage events that result in the formation of fragments of the full-length nascent polypeptide. A fragment, or physical association of fragments may have the full biological activity associated with hDRR4 or hDRR7; however, the degree of receptor activity may vary between individual receptor fragments and physically associated receptor polypeptide fragments.

Therefore, in another aspect this invention provides modified hDRR polypeptides which have amino acid deletions, additions or substitutions but that still retain substantially the same biological activity, i.e., binding EPF or EPF-related peptides, as the native hDRR polypeptide. A hDRR polypeptide has "substantially the same biological activity" as the wild type if that polypeptide has an $EC_{50}$-value for the EPF-related peptide encoded by amino acid sequence SEQ ID No:8, that is no more than 10-fold, preferably no more than 5-fold greater than the $EC_{50}$-value of the wild type hDRR receptor polypeptide for the same ligand. For the hDRR4 receptor an $EC_{50}$-value ranging of 10.6-12 nM has been determined for the EPF-related peptide consisting of SEQ ID NO:8. For the hDRR7 receptor an $EC_{50}$-value ranging of 345-82.9 nM has been determined for the EPF-related peptide consisting of SEQ ID NO:8

The present invention also provides antibodies against and epitopes of EPF and the EPF-related peptides according to the invention, including antisera and both polyclonal and monoclonal embodiments of such antibodies and hybridoma cell lines producing such monoclonal antibodies. Antibodies generated against polypeptides of the present invention may be obtained by administering the polypeptides or epitope-bearing fragments, or cells to an animal, preferably non-human animal using routine protocols The above-described antibodies may be employed to purify the polypeptides according to the invention by affinity chromatography or to treat diseases of the invention. It is also an object of the present invention to provide the use of the aforementioned antibodies in a method of diagnosing a pathological condition in a subject related to a disorder related to hDRR activity comprising; contacting the antibodies with a test sample wherein said test preferably consists of bodily fluids such as blood, saliva, semen, cerebrospinal fluid, plasma or lymph; and measuring the reactivity of said antibodies on the test sample.

The reactivities of antibodies on a sample may be determined by any appropriate means. Tagging with individual reporter molecules is one possibility. Said reporter molecules may directly or indirectly generate detectable, and preferably measurable, signals.

Thus in another aspect, the present invention relates to a diagnostic kit comprising;
  i) a polypeptide of the present invention, preferably the polypeptides selected from the group consisting of SEQ ID NO:18, SEQ ID NO:19, SEQ ID NO:20 and SEQ ID NO:21, or of the hDRR4 binding fragment encoded by SEQ ID NO:8; or ii) an antibody to a polypeptide of the present invention preferably a polypeptide selected from the group consisting of SEQ ID NO:18, SEQ ID NO:19, SEQ ID NO:20 and SEQ ID NO:21, or of the hDRR4 binding fragment encoded by SEQ ID NO:8.

It will be appreciated that in any such kit, i) or ii) may comprise a substantial component Such a kit will be of use in diagnosing a disease or susceptibility to a disease, particularly diseases of the invention.

Recombinant Expression of hDRR Receptor Polypeptides

An important aspect of many assays is the step of providing a host cell expressing a recombinant hDRR receptor on the surface thereof. Therefore, in a further aspect the present invention relates to hDRR expression vectors that can be used in an assay according to the invention.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, cyanobacteria, plant cells, insect cells, fungal cells including yeast cells, and animal cells including human cells.

Specifically designed vectors allow the shuttling of DNA between hosts such as bacteria-yeast or bacteria-animal cells or bacteria-fungal cells or bacteria-invertebrate cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

The isolated and purified nucleic acid molecules, according to the invention, encoding hDRR4 or hDRR7 may be cloned into an expression vector for expression in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to *Drosophila*- and silkworm-derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, neuroblastoma, glial cells and HEK-293 (ATCC CRL1573).

Therefore, in a further embodiment this invention relates to the use of a recombinant host cell containing a recombinantly cloned nucleic acid molecule encoding a hDRR protein or fragments thereof in an assay according to the invention. In a further aspect the recombinant host cell contains a nucleic acid molecule which is either genomic DNA or has a nucleotide sequence consisting of: (SEQ ID NO:1) and fragments thereof.

In a more preferred embodiment of this invention the recombinant host cell consists of the HEK293 cells comprising the nucleotide sequence consisting of Seq ID NO:1 or fragments thereof, in the mammalian expression vector pcDNA3.

The expression vector may be introduced into host cells via any one of a number of techniques including but not limited to transformation, transfection, protoplast fusion, lipofection, and electroporation. The expression vector-containing cells are clonally propagated and analyzed to determine whether they produce a hDRR4 protein. Identification of receptor expressing host cell clones may be done by several means, including but not limited to immunological reactivity with antibodies directed against the polypeptides according to the invention, and the presence of host cell-associated hDRR4 activity.

The proteins of this invention may be synthesized either by direct expression or as a fusion protein comprising the protein of interest as a translational fusion with another protein or peptide which may be removable by self, enzymatic or chemical cleavage. Therefore, in a particular embodiment this invention provides the proteins according to the invention wherein said polypeptides are part of a fusion protein.

Furthermore, one could use, e.g., a mammalian cell that already comprises in its genome a nucleic acid molecule encoding a DRR polypeptide as described above, but does not express the same or not in an appropriate manner due to, e.g., a weak promoter, and introduce into the mammalian cell a regulatory sequence such as a strong promoter in close proximity to the endogenous nucleic acid molecule encoding said receptor polypeptide so as to induce expression of the same.

As such a recombinant host cell containing a polynucleotide encoding a DRR polypeptide under the control of a heterologous transcription and/or regulatory sequence or protein, would be another embodiment of this invention.

In this context the term "regulatory sequence" denotes a nucleic acid molecule that can be used to increase the expression of the DRR receptor polypeptide, due to its integration into the genome of a cell in close proximity to the DRR receptor encoding gene. Such regulatory sequences comprise promoters, enhancers, inactivated silencer intron sequences, 3'UTR and/or 5'UTR coding regions, protein and/or RNA stabilizing elements, nucleic acid molecules encoding a regulatory protein, e.g., a transcription factor, capable of inducing or triggering the expression of the DRR receptor gene or other gene expression control elements which are known to activate gene expression and/or increase the amount of the gene product. The introduction of said regulatory sequence leads to increase and/or induction of expression of DRR receptor polypeptides, resulting in the end in an increased amount of DRR receptor polypeptides in the cell. Thus, the present invention is aiming at providing de novo and/or increased expression of DRR receptor polypeptides.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis, Basic Methods In Molecular Biology (1986).

In addition, expression of polynucleotides according to the invention may also be performed using in vitro produced synthetic mRNA. Synthetic mRNA or mRNA isolated from hDRR producing cells can be efficiently translated in various cell-free systems, including but not limited to wheat germ extracts and reticulocyte extracts, as well as efficiently translated in cell-based systems, including but not limited to microinjection into frog or toad oocytes (*Xenopus laevis*), with microinjection into toad oocytes being generally preferred.

Assays

Assays of the present invention can be designed in many formats generally known in the art of screening compounds for biological activity or for binding receptors.

Polypeptides of the present invention are responsible for one or more biological functions, including one or more disease states, in particular the diseases hereinbefore mentioned. It is therefore desirable to devise screening methods to identify compounds which stimulate or which inhibit the function of hDRR receptors.

The assays of the present invention advantageously exploit the fact that EPF or EPF-related peptides are high affinity ligands for hDRR receptor polypeptides and activate the hDRR receptors upon binding thereto.

Therefore, the present invention includes methods of identifying compounds that specifically bind to hDRR receptor polypeptides, wherein said compounds may be ligands, agonists or antagonists of the hDRR receptor polypeptide. The assay methods of the present invention differ from those described in the art because the present assays incorporate at least one step wherein the interaction of EPF or EPF-related peptides with the hDRR receptor is incorporated in the assay. The specificity of binding can be shown by measuring the affinity of the compounds for cells expressing a hDRR receptor polypeptide on the surface thereof or affinity for membranes of such cells.

Thus, the present invention provides for a method of identifying and obtaining a test compound capable of binding a hDRR receptor comprising:
 a) incubating a source containing a hDRR or a fragments thereof, with
  i) EPF or EPF-related peptides
  ii) said test compound; and
 b) measuring the effect of the test compound on the amount of EPF or EPF-related peptides bound to the receptor.

In a preferred embodiment, the present invention provides for a method of identifying and obtaining a test compound capable of binding the hDRR4 receptor comprising:
 a) incubating a source containing hDRR4 or a fragments thereof, with
  i) EPF or EPF-related peptides
  ii) said test compound; and
 b) measuring the effect of the test compound on the amount of EPF or EPF-related peptides bound to the receptor.

In a further embodiment of the present invention, the hDRR4 containing source is selected from the group consisting of;
 i) an isolated and purified protein having the amino acid sequence of SEQ ID NO:2 or a fragment thereof;
 ii) cells expressing on the surface thereof the polypeptide receptor having the amino acid sequence of SEQ ID NO:2 or a fragment thereof; or
 iii) membrane preparations of cells expressing on the surface thereof the polypeptide receptor having the amino acid sequence of SEQ ID NO:2 or fragments thereof.

In a another embodiment, the present invention provides for a method of identifying and obtaining a test compound capable of binding the hDRR7 receptor comprising:
 a) incubating a source containing hDRR7 or a fragments thereof, with
  i) EPF or EPF-related peptides
  ii) said test compound; and
 b) measuring the effect of the test compound on the amount of EPF or EPF-related peptides bound to the receptor.

In a further embodiment of the present invention, the hDRR7 containing source is selected from the group consisting of;

i) an isolated and purified protein having the amino acid sequence of SEQ ID NO:12 or a fragment thereof;
ii) cells expressing on the surface thereof the polypeptide receptor having the amino acid sequence of SEQ ID NO:12 or a fragment thereof; or
iii) membrane preparations of cells expressing on the surface thereof the polypeptide receptor having the amino acid sequence of SEQ ID NO:12 or fragments thereof.

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. In a preferred embodiment, this labeled competitor is a ligand known to bind to hDRRs such as EPF, also known as chaperonin 10, or EPF-related peptides. In a further embodiment said EPF-related peptide consists of the hDRR binding fragment encoded by SEQ ID NO:8 or of the EPF-related peptides encoded by SEQ ID NO:18, SEQ ID NO:19, SEQ ID NO:20 or SEQ ID NO:21.

Therefore, in a more preferred embodiment, the screening method comprises labeled EPF or labeled EPF-related peptides, wherein said label is used to measure the effect of the test compound on the amount of EPF or EPF-related peptide bound to the receptor.

Accordingly, the present invention provides a method of identifying and obtaining a test compound capable of binding the hDRR4 receptor comprising:
i) membrane preparations of cells, preferably HEK293 cells, expressing on the surface thereof the receptor polypeptide having the amino acid sequence of SEQ ID NO:2;
ii) incubating said membranes with a labeled EPF-related peptide comprising an amino acid sequence encoded by SEQ ID NO:8, SEQ ID NO:18, SEQ ID NO:19, SEQ ID NO:20 or SEQ ID NO:21, preferably iodinated EPF-related peptide consisting of SEQ ID NO:8;
iii) adding the test compound to the incubation mixture; and
iv) measuring the effect of the test compound on the amount of labeled EPF-related peptide bound to the hDRR4 receptor.

Concordantly, the present invention provides a method of identifying and obtaining a test compound capable of binding the hDRR7 receptor comprising:
i) membrane preparations of cells, preferably HEK293 cells, expressing on the surface thereof the receptor polypeptide having the amino acid sequence of SEQ ID NO:12;
ii) incubating said membranes with a labeled EPF-related peptide comprising the amino acid sequence encoded by an amino acid sequence encoded by SEQ ID NO:8, SEQ ID NO:18, SEQ ID NO:19, SEQ ID NO:20 or SEQ ID NO:2, preferably iodinated EPF-related peptide consisting of SEQ ID NO:8;
iii) adding the test compound to the incubation mixture; and
iv) measuring the effect of the test compound on the amount of labeled EPF-related peptide bound to the hDRR7 receptor.

Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active receptor polypeptides may be employed in screening methods for inverse agonists or inhibitors, in the absence of an agonist or inhibitor, by testing whether the candidate compound results in inhibition or activation of the polypeptide.

Therefore, the present invention provides a method of identifying and obtaining a test compound capable of modulating the activity of the hDRR receptor comprising:
a) incubating a source containing hDRR or functional fragments thereof, with said test compound;
b) measuring the effect of the test compound on the activity of the hDRR receptor; and
c) compare this effect with the activity of the hDRR receptor upon binding of EPF or EPF-related peptides.

In a further embodiment of the present invention, the hDRR-containing source in a method of identifying and obtaining a test compound capable of modulating the activity of a hDRR receptor, is a cell expressing on the surface thereof the polypeptide receptor having the amino acid sequence of SEQ ID NO:2 or SEQ ID NO:12. In a preferred embodiment said cell may be a recombinant host cell containing a recombinantly cloned nucleic acid molecule encoding a hDRR4 or a hDRR7 protein or fragments thereof as provided in above-described methods. The effect of the modulator on a hDRR receptor may be modulation of an intracellular second messenger formation that is mediated by hDRR receptors such as intracellular calcium, cAMP or a reporter gene product. hDRR belongs to the class of proteins known as G-protein coupled receptors (GPCRs). GPCRs transmit signals across cell membranes upon the binding of the ligand. The ligand-bound GPCR activates intracellular signalling events mediated by heterotrimeric G proteins, such as activation of the adenylate cyclase pathway or activation of the phospholipase C-β pathway. Assay to assess the activation of the aforementioned intracellular signalling events are generally known in the art and include amongst others cell based assays for signal transduction comprising chimeric ligand-inducible transcription factors, binding assays for G-protein-coupled receptors using fluorescence intensity distribution analysis, cell-signaling assays using cyclic nucleotides coupled to luminophores or measurement of responses from G protein coupled receptors using a multiple response element or cAMP response element-directed reporter assay.

Accordingly, the present invention provides a method of identifying and obtaining a test compound capable of modulating the activity of the hDRR4 receptor comprising:
a) incubating a source containing hDRR4 or functional fragments thereof, with said test compound;
b) measuring the effect of the test compound on the activity of the hDRR4 receptor; and
c) compare this effect with the activity of the hDRR4 receptor upon binding of EPF or EPF-related peptides.

In a preferred embodiment, the present invention provides a method of identifying and obtaining a test compound capable of modulating the activity of the hDRR4 receptor consisting of;
a) host cells, preferably HEK293 cells, co-transfected with a mammalian expression vector, preferably pcDNA3, encoding the hDRR4 receptor protein consisting of SEQ ID NO:2 and a mammalian expression vector, preferably pcDNA3, encoding Gα16 consisting of SEQ ID NO:10;
b) loading the cells with a calcium sensitive fluorescent dye such as Fura-2, FLUO-3 or FLUO-4, preferably FLUO-3 or FLUO-4;

c) incubating the cells with the test compound;
d) measure the effect of the test compound on the hDRR4 receptor activity as a change in relative fluorescence units of the calcium sensitive fluorescent dye; and
e) compare the effect with the activity of the hDRR4 receptor upon binding of EPF or EPF-related peptides.

In another preferred embodiment, the method to identify and obtain a compound capable of modulating the activity of the hDRR4 receptor consists of;
a) host cells, preferably HEK293 cells, transfected with a mammalian expression vector, preferably pcDNA3, encoding the hDRR4 receptor protein consisting of SEQ ID NO:2;
b) loading the cells with a calcium sensitive fluorescent dye such as Fura-2, FLUO-3 or FLUO-4, preferably FLUO-3 or FLUO-4, preferably FLUO-4;
c) incubating the cells with the test compound;
d) measure the effect of the test compound on the hDRR4 receptor activity as a change in relative fluorescence units of the calcium sensitive fluorescent dye; and
e) compare the effect with the activity of the hDRR4 receptor upon binding of EPF or EPF-related peptides.

Accordingly, the present invention provides a method of identifying and obtaining a test compound capable of modulating the activity of the hDRR7 receptor comprising:
a) incubating a source containing hDRR7 or functional fragments thereof, with said test compound;
b) measuring the effect of the test compound on the activity of the hDRR7 receptor; and
c) compare this effect with the activity of the hDRR7 receptor upon binding of EPF or EPF-related peptides.

In a preferred embodiment, the present invention provides a method of identifying and obtaining a test compound capable of modulating the activity of the hDRR7 receptor consisting of;
a) host cells, preferably HEK293 cells, co-transfected with a mammalian expression vector, preferably pcDNA3, encoding the hDRR7 receptor protein consisting of SEQ ID NO:12 and a mammalian expression vector, preferably pcDNA3, encoding Gα16 consisting of SEQ ID NO:10;
b) loading the cells with a calcium sensitive fluorescent dye, preferably FLUO-4;
c) incubating the cells with the test compound;
d) measure the effect of the test compound on the hDRR7 receptor activity as a change in relative fluorescence units of the calcium sensitive fluorescent dye; and
e) compare the effect with the activity of the hDRR7 receptor upon binding of EPF or EPF-related peptides.

In another preferred embodiment, the method to identify and obtain a compound capable of modulating the activity of the hDRR7 receptor consists of;
a) host cells, preferably HEK293 cells, transfected with a mammalian expression vector, preferably pcDNA3, encoding the hDRR7 receptor protein consisting of SEQ ID NO:12;
b) loading the cells with a calcium sensitive fluorescent dye, preferably FLUO-4;
c) incubating the cells with the test compound;
d) measure the effect of the test compound on the hDRR7 receptor activity as a change in relative fluorescence units of the calcium sensitive fluorescent dye; and
e) compare the effect with the activity of the hDRR7 receptor upon binding of EPF or EPF-related peptides.

It will be readily appreciated by the skilled artisan that the discovery of the interaction of EPF or EPF-related peptides with hDRR may also be used in a method for the structure-based or rational design of an agonist or antagonist of the polypeptide, by:
a) probing the structure of the ligand binding site on hDRR with EPF or EPF derivatives;
b) identifying contacting atoms in the ligand binding site of the hDRR receptor that interact with the EPF ligand during binding;
c) design test compounds that interact with the atoms identified in (b) to modulate the activity of the hDRR receptor, and
d) contact said designed test compound with a source containing hDRR or a functional fragment thereof, to measure the capability of said compound to modulate the hDRR activity.

It will be further appreciated that this will normally be an iterative process.

Therapeutic Use

In general, agonists or antagonists may be employed for therapeutic and prophylactic purposes for such diseases as hereinbefore mentioned. Compounds may be identified from a variety of sources, for example, cells, cell-free preparations, chemical libraries, and natural product mixtures. Such agonists or antagonists so-identified may be natural or modified peptides, ligands, enzymes, etc., as the case may be, of the receptor polypeptide; or may be structural or functional mimetics thereof (see Coligan et al., *Current Protocols in Immunology* 1 (2):Chapter 5 (1991)).

Therefore, the present invention relates to the use of EPF, EPF fragments or the EPF-related peptides as a medicine and where said EPF, EPF fragments or EPF-related peptide is an agonists of the hDRR receptor, for use in the treatment of pain or in the treatment of autoimmune diseases like rheumatoid arthritis, multiple sclerosis or other conditions where immunosuppresive actions are desired like in IBD or to prevent transplant rejection. In a preferred embodiment said EPF, EPF fragments or EPF-related peptide consists of the hDRR binding fragment encoded by SEQ ID NO:8 or a EPF-related peptide according to the invention, i.e consisting of a polypeptide selected from the group consisting of SEQ ID NO:18, SEQ ID NO:19, SEQ ID NO:20 or SEQ ID NO:21.

Therefore, the present invention further relates to a compound identified in an assay according to the invention, wherein said compound is capable of binding and/or modulating the hDRR receptor activity and wherein said compound is either an agonist or antagonist of the receptor as determined in any of the above described assays. It further relates to the use of said compounds as a medicine and where said compound is an agonist for use in the treatment of pain or autoimmune diseases like rheumatoid arthritis, multiple sclerosis or other conditions where immunosuppresive actions are desired like in IBD or to prevent transplant rejection. Where said compound is an antagonist of the hDRR receptor polypeptide, the compound may be used as contraceptive, in the prevention of foetal loss or in the treatment of cell-proliferative disorders such as cancer.

Also provided is the use of a compound identified in an assay according to the invention, wherein said compound is capable of binding and/or modulating the hDRR4 receptor activity and wherein said compound is either an agonist or antagonist of the receptor as determined in any of the above described assays. It further relates to the use of said compounds hDRR4 specific compounds as a medicine and where said compound is an agonist for use in the treatment of pain.

Likewise, the present invention provides the use of a compound identified in an assay according to the invention, wherein said compound is capable of binding and/or modulating the hDRR7 receptor activity and wherein said compound is either an agonist or antagonist of the receptor as determined in any of the above described assays. It further relates to the use of said compounds as a medicine and where said compound is an agonist for use in the treatment of autoimmune diseases like rheumatoid arthritis, multiple sclerosis or other conditions where immunosuppresive actions are desired like in IBD or to prevent transplant rejection. Where said compound is an antagonist of the hDRR7 receptor polypeptide, the compound may be used as contraceptive, in the prevention of foetal loss or in the treatment of cell-proliferative disorders such as cancer.

Thus, in a further aspect, the present invention provides a method for preventing, treating or ameliorating a medical condition related to a disorder of hDRR activity which comprises administering to a mammalian subject a therapeutically effective amount of a hDRR modulating compound as described above, including the EPF-related peptides, optionally in combination with a pharmaceutically acceptable carrier, in an amount effective to modulate the hDRR receptor activity. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

It is thus an object of the present to provide a method for preventing, treating or ameliorating autoimmune diseases like rheumatoid arthritis, multiple sclerosis or other conditions where immunosuppresive actions are desired like in IBD or to prevent transplant rejection, comprising administering to a mammalian subject an effect amount of a hDRR7 receptor agonist identified using one of the above described assays. Accordingly the present invention provides a method for preventing, treating or ameliorating cell proliferative disorders such as cancer, comprising administering to a mammalian subject an effect amount of a hDRR7 receptor antagonist identified using one of the above described assays. It is a further object of the invention to provide a method for preventing, treating or ameliorating the transmission, modulation and sensation of pain, comprising administering to a mammalian subject an effect amount of a hDRR4 receptor agonist identified using one of the above described assays.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of patches, salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1-100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLE 1

Cloning and Functional Characterization of the GPCR HDRR4

Material and Methods

Materials

Expand high fidelity polymerase, PCR buffer, T4 DNA ligase, and restriction endonucleases were obtained from Boehringer (Mannheim, Germany). Oligonucleotides were purchased from Eurogentec (Seraing, Belgium). Plasmid preparation kits and the Qiaquick PCR amplification kit were from Qiagen (Hilden, Germany). The PRISM Ready Reaction Dye Terminator Cycle Sequencing kits and the ABI 377 or 373A sequencing machines were from Applied Biosystems (Foster City, Calif., U.S.A.). The Geneamp PCR System 9600 was from Perkin-Elmer (Norwalk, Conn., U.S.A.). The mammalian expression vector pcDNA3 was obtained from Invitrogen (Carlsbad, Calif., U.S.A.). Dulbecco's modified Eagle medium (DMEM), foetal calf serum, and dialysed foetal calf serum were from Life Technologies (Gaithersburg, Md., U.S.A.).

DNA Sequencing

DNA sequencing was carried out with reagents from the ABI PRISM BigDye Terminator Cycle Sequencing Ready Reaction Kit (PE Biosystems) on PTC-200 PCR machines (MJ Research). Reaction products were purified on SEQueaky Kleen 96 well Terminator Removal Kit columns (BioRad) and were resolved on ABI377 DNA sequencing machines. For sequence analysis we used the Sequencher software from GeneCodes (Ann Harbor, Mich.).

Cloning of hDRR4

PCR was performed on a human genomic cosmid library (Clontech, Palo Alto, Calif., USA) using a forward primer (GGAATTCGCCACCATGGATCCAACGGTCTCAA) (SEQ ID NO:25 and a reverse primer (GTCTCGAGTCACTGCTCCAATCTGCTTCCC) (SEQ ID NO: 6). The resulting PCR products were cloned with the help of the TOPO™ TA Cloning kit (Invitrogen, Carlsbad, Calif. U.S.A). The full length reading frame was inserted into the mammalian expression vector pcDNA3 (Invitrogen, Carlsbad, Calif., U.S.A.) and was used in subsequent screening experiments.

Cloning of hDRR7

PCR was performed on a human genomic cosmid library (Clontech, Palo Alto, Calif., USA) using the hDRR7 forward primer (CGAATTCCGCCACCATGGATCCAACCAC-CCCGG) (SEQ ID NO:13) and the hDRR7 reverse primer (GCTCTAGAGGCTGTCCATCTCTACACCAGACTGC) (SEQ ID NO:14). The resulting PCR product was inserted into the mammalian expression vector pcDNA3 (Invitrogen, Carlsbad, Calif., U.S.A.) and was used in subsequent screening experiments.

Transient Expression in Mammalian Cells and FLIPR Assay

The hDRR4 expression plasmid or the hDRR7 expression plasmid was transiently co-transfected with a Gα16-pcDNA3 contruct using the FuGENE 6 reagent (Roche Molecular Biochemicals, Mannheim, Germany) into HEK293 cells. The cells were loaded with Fluo-4 (Molecular Probes, Eugene, Oreg., U.S.A.) according to the recommendations of the supplier. Subsequently the cells were assayed in the FLIPR instrument (Molecular Devices, Sunnyvale, Calif., U.S.A.) for $Ca^{2+}$ transients.

Preparation of Tissue Extracts and Extract Fractionation

Five kg porcine hypothalamus were homogenized and extracted in methanol/water/acetic acid, 90/9/1, v/v/v. After centrifugation, the supernatant was delipidated by n-hexane extraction and the aqueous layer was fractionated by a Megabondelute fractionation. The material eluting at 50% acetonitrile/$H_2O$ was further fractionated on a HPLC C18 column. The fractions derived thereof were tested for activation of the hDRR4 GPCR in the FLIPR assay. The Megabondelute fraction eluting from 0 to 60% acetonitrile in aqueous trifluoracetic acid (0.1%) was further fractionated on a preparative DeltaPak C18 column (Waters Ass., 25×100 mm, 15 μm, 300 Å). The fractions derived thereof were tested for activation of the hDRR4 GPCR in the FLIPR assay. Subsequent purification steps on a preparative Hypersil C18, an analytical Symmetry C18 column (4.6×250 mm), a narrow bore Xterra C8 column (2.1×250 mm), a narrow bore Xterra C18 column (2.1×250 mm) column and finally a narrow bore Symmetry C18 column (2.1×150 mm) were also followed by the FLIPR based activity assay for fractions activating hDRR4 transfected cells.

Mass Spectrometry and Edman Degradation Based Sequencing

Electrospray ionisation (ESI) double quadrupole (Qq) orthogonal acceleration (oa) time-of-flight (Tof) mass spectrometry was performed on a Q-Tof system (Micromass UK). The active molecule was identified by analysis of fragment ions using collision induced dissociation (CID). One μl of acetonitrile/water/formic acid (50/49.9/0.1, v,v,v) containing the active fraction was loaded in a gold coated capillary (Protana L/Q needle). The needle voltage was set at 900 V, the sampling cone at 25 V. The sample was sprayed at a flow rate of about 25 nl/min giving extended analysis time during which MS as well as MS/MS spectra could be acquired. During MS/MS or tandem mass spectromety fragment ions are generated from a selected precursor ion by collision induced dissociation (CID), the collision energy is typically varied between 20 and 35 V, Argon was used as the collision gas. N-terminal amino acid sequencing of the purified peptide was performed on a Perkin Elmer/Applied Biosystems Procise 492 micro-sequencer running in the pulsed mode.

Membrane Preparation

The membranes were prepared as total particulate fractions. The cell lines were cultured to 90% confluency on 145 mm petri dishes and treated with 5 mM sodium butyrate, 24 hours before collection. The culturing medium was removed and the cells were washed twice with ice-cold phosphate-buffered saline (PBS w/o $Ca^{2+}$ and $Mg^{2+}$), scraped from the plates in 50 mM Tris-HCl buffer, pH 7.4, and collected by centrifugation (10 minutes at 16,000 RPM at 4° C.). The cell pellet was re-suspended in hypotonic 5 mM Tris-HCl buffer, pH 7.4, and homogenized with an Ultra Turrax homogenizer. The homogenate was centrifuged at 18,000 RPM for 20 minutes at 4° C. The final pellet was re-suspended in 50 mM Tris-HCl buffer, pH 7.4 and stored in aliquots at −70° C. A protein determination was performed using the Bradford protein assay (Biorad) using bovine serum albumin (BSA) as standard.

[$^3$H]Adenine Binding

[$^3$]Adenine binding experiments were performed to characterize transiently transfected cell lines. Membranes were thawed on ice and diluted in 50 mM HEPES buffer, pH 7.4 supplemented with 10 mM $MgCl_2$ and 1 mM EGTA. Non-specific binding was defined in the presence of 1 μM adenine and a 1 hour incubation at 25° C. with [$^3$H]adenine (specific activity of 30.4 Ci/mmol), was found to be optimal for competition binding assays. Assays were carried out in a final volume of 500 μl, using 20 μg of membrane protein for the transfected as well as the wildtype COS cells. The reaction was terminated by rapid filtration through Whatman GF/B filters using a Brandel multi-channel cell harvester (96 wells). The filters were washed three times with 3 ml ice cold 50 mM HEPES buffer, pH 7.4, transferred to liquid scintillation vials and 3 ml of scintillation fluid (Ultima Gold MV) was added. Samples were counted in a β-scintillation counter after at least 6 hours to permit the glass fiber filters to become uniformly translucent.

Competitive inhibition of [$^3$H]adenine by adenine was performed with 15 nM of [$^3$H]adenine.

Specific binding was calculated as difference between counts in the presence and absence of 1 μM unlabeled adenine.

Verify Expression Levels of Genes Via Real-time Quantification PCR

RNA from various tissues was obtained from Clontech except the Dorsal Root Ganglia RNA which was obtained from Analytical Biological Services. SDS primers and Taq-Man probes for the hDRR4 gene have been designed using PrimerExpress 1.0 software (Perkin Elmer, Mass., USA). The SDS forward and reverse primers for the hDRR4 gene were 5'-GCGCAGGAACGCCTTCT-3' (SEQ ID NO:22) and 5'-CGGCCGCTGAGGAAGAG-3' (SEQ ID NO:23), respectively. The TaqMan probe for hDRR4 (5'-TCCTCAACTTG-GCCGCAGCAGA-3' (SEQ ID NO:24) has been designed using PrimerExpress 1.0 software (Perkin Elmer, Mass., USA) and can be chosen either from the upper strand or the lower strand of the target sequence. The TagMan hDRR4 probe has been labeled with a reporter fluorescent dye, 6-carboxyfluorescein (FAM) at the 5' end.

cDNA was made using Superscript II Reverse transcriptase. RT was carried out for 60 min at 42° C. in a water bath. The reaction was terminated by heating at 70° C. for 10 min. The PCR amplification was then performed in MicroAmp Optical 96-well reaction plates for 50 cycles with each cycle at 95° C. for 15 s and 60° C. for 1 min. All reactions were carried out in triplicate using the ABI Prism 7700 SDS. Relative expression of hDRR4 in the tested tissues was compared to CyclophilinA expression.

Results

Generation and cDNA Sequence of hDRR4

After performing PCR on a human genomic cosmid library a single PCR products was obtained. Sequencing of the PCR product showed strong similarity with the sequences of hDRR3 (97% aa identity) and hDRR4 (99% aa identity) (Patent W9932519). However, the sequence was identical to a stretch of sequence in an entry in the EMBL database (AC023078). We arrived at the nucleotide and amino acid sequence depicted in FIG. 1.

The sequence described in FIG. 1 was analysed by BLAST (Altschul et al., 1997) search to examine whether related GPCRs with known ligands could be found. The closest homologues of this orphan GPCR that was retrieved, was the GPCR RC56.3.1 recently identified in our laboratory as an adenine receptor. No ligands have been reported for other receptors related to hDRR4. These are a family of human GPCRs (Derwent sequence database accession numbers Z10067, Z10068, Z10069, Z10070 Z10071 and Z10072) cloned from dorsal root ganglion that have between 79% and 99% of residues in common with GPCR hDRR4. Another well known homologue is the mas proto-oncogene which shares 38% of residues with hDRR4.

Our first approach was to test adenine and other structurally related compounds, especially purines on hDRR4 in a FLIPR-based cellular assay. This was done by transient transfections in HEK293 cells with and without co-transfection of chimeric G proteins or the promiscuous Gα16 G protein. In these assays no specific response was observed. In a binding experiment using tritiated adenine no specific adenine binding to hDRR4 could be detected, while RC56.1.3 transfected cells showed clear specific adenine binding. Since this approach did not give us a hint for the natural ligand of this receptor we applied in order to identify the natural ligand the 'reverse pharmacology' strategy.

Purification of the Natural Agonist of hDRR4 from Porcine Hypothalamus

Essentially, an extract from the tissue known to be a rich source of secreted peptides, e.g. hypothalamus was prepared and the purification of the natural ligand was followed by a cellular assay based on the activation of the orphan GPCR as described in Material and Methods.

The screening of the porcine hypothalamus extract after the first fractionation on a C18 column delivered a range of fractions that resulted in transient intracellular $Ca^{2+}$ release for cells transiently transfected with the hDRR4 expression construct. This was the case for HEK293 cells transiently co-transfected with a Gα16 expression construct (FIG. 2), but not for wild-type HEK293 cells (data not shown). Two of these fractions, number 65 and 66, that yielded the strongest stimulation were chosen for further sub-fractionation and processed as described in Material and Methods. The purification was guided by the FLIPR based activity assay and the fraction that showed activity from the last column run was subjected to mass spectrometry to determine purity as well as the structure of the compounds that it contained.

Identification of hDRR4 Activating Substance by Mass Spectrometry

Mass analysis of the active purified fraction from the Symmetry C18 (4.6×250 mm; 5 µm, Waters) reverse phase column gave one major mass-peak at 2163 Da (2164.7 M+H$^+$) The elution profile of the active fraction on different HPLC columns indicated that the receptor-activating compound was a peptide. Therefore, this mass was subsequently analyzed by Edman degradation based sequencing. The sequence was determined to be:

AFRKFLPLFDRVLVERSA (SEQ ID NO: 8)

(in single letter amino acid annotation).

Effect of the hDRR4 Activating Substance on the Cell Based FLIPR Assay

Figure 3:
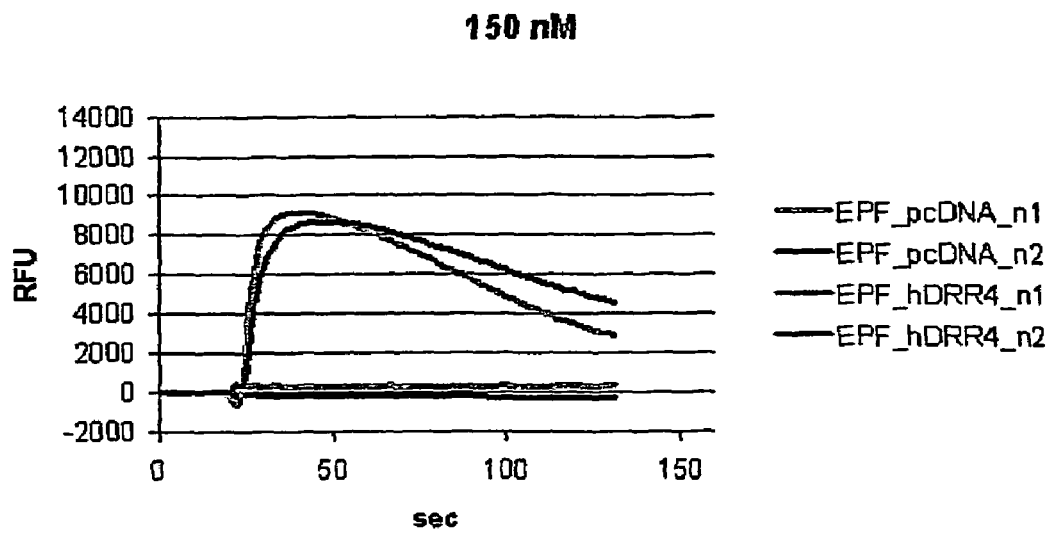
FIG. 3—Activation of orphan GPCR hDRR4 (SEQ ID NO:2) by the hDRR binding fragment of EPF (SEQ ID NO:8) at a test concentration of 150 nM after transient co-transfection with Gα16-pcDNA into Hek293. Relative fluorescence units (RFU) were determined by loading the cells with Fluo-4 (Molecular Probes, Eugene, Oreg., U.S.A.)
Figure 7:
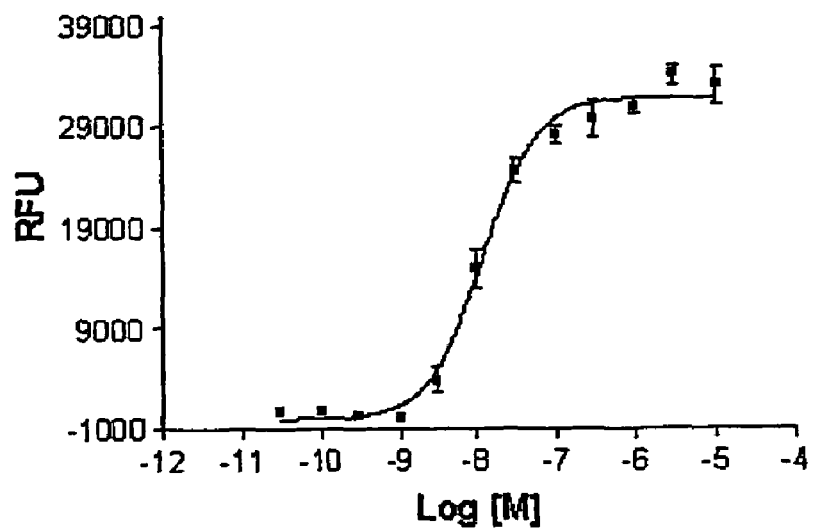
FIG. 7—Dose response curve of the hDRR binding fragment of EPF (SEQ ID NO:8) on the hDRR4 receptor as determined using the FLIPR calcium assay.

Activation of orphan GPCR hDRR4 (SEQ ID NO:2) by the hDRR binding fragment of EPF (SEQ ID NO:8) at a test concentration of 150 nM was measured in Hek293 cells co-transfected with Gα16-pcDNA. Relative fluorescence units (RFU) were determined by loading the cells with Fluo-4 (Molecular Probes, Eugene, Oreg., U.S.A.). Hek 293 cells only transfected with the Gα16 pcDNA expression vector did not response to the hDRR binding fragment as shown in FIG. 3. Using this FLIPR assay at different test concentrations of the hDRR activating peptide consisting of SEQ ID NO:8, an $EC_{50}$-value of 12 nM has been determined (FIG. 7).

Expression of the hDRR4 Gene

Figure 6:
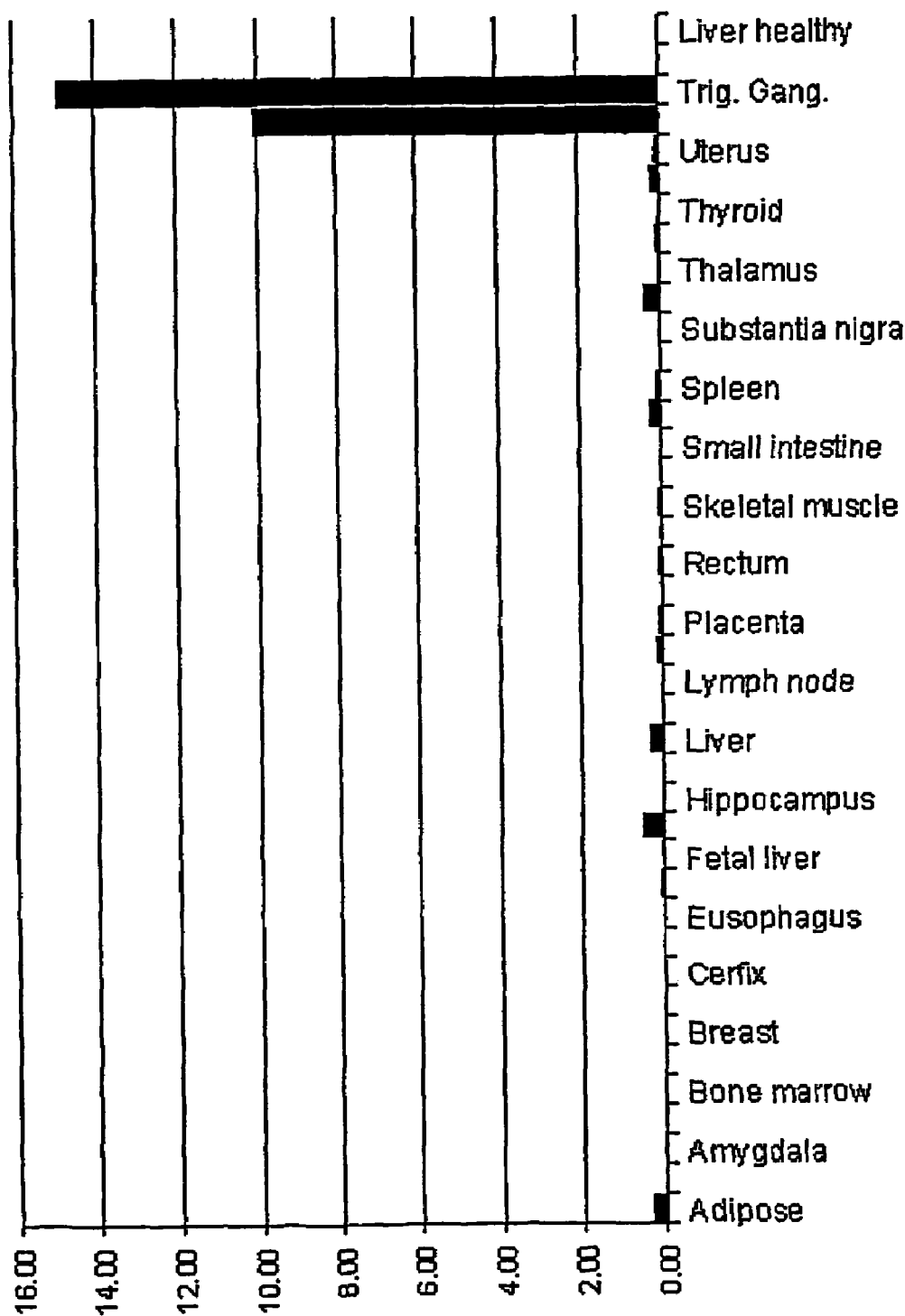
FIG. 6—Relative expression of hDRR4 in a number of tissues compared to the relative expression of human cyclophilin A in the evaluated tissues. Expression levels were determined using real time quantitative PCR.

Real-time quantification PCR, revealed hDRR4 expression in dorsal root ganglia (DRG) and trigeminal ganglia. This finding substantiates the potential role of this receptor in perception or modulation of pain. Of al the tissues tested, hDRR4 was almost exclusively expressed in dorsal root ganglia and trigeminal ganglia as shown in FIG. 6 herein the expression levels in the other tissues were compared to the expression level observed in dorsal root ganglia and trigeminal ganglia.

EXAMPLE 2

Cloning and Functional Characterization of the GPCR HDRR7

Material and Methods

Materials

Expand high fidelity polymerase, PCR buffer, T4 DNA ligase, and restriction endonucleases were obtained from Boehringer (Mannheim, Germany). Oligonucleotides were purchased from Eurogentec (Seraing, Belgium). Plasmid preparation kits and the Qiaquick PCR amplification kit were from Qiagen (Hilden, Germany). The PRISM Ready Reaction Dye Terminator Cycle Sequencing kits and the ABI 377 or 373A sequencing machines were from Applied Biosystems (Foster City, Calif., U.S.A.). The Geneamp PCR System 9600 was from Perkin-Elmer (Norwalk, Conn., U.S.A.). The mammalian expression vector pcDNA3 was obtained from Invitrogen (Carlsbad, Calif., U.S.A.). Dulbecco's modified Eagle medium (DMEM), foetal calf serum, and dialysed foetal calf serum was from Life Technologies (Gaithersburg, Md., U.S.A.).

DNA Sequencing

DNA sequencing was carried out with reagents from the ABI PRISM BigDye Terminator Cycle Sequencing Ready Reaction Kit (PE Biosystems) on PTC-200 PCR machines (MJ Research). Reaction products were purified on SEQueaky Kleen 96 well Terminator Removal Kit columns (BioRad) and were resolved on ABI377 DNA sequencing machines. For sequence analysis we used the Sequencher software from GeneCodes (Ann Harbor, Mich.).

Cloning of hDRR7

PCR was performed on a human genomic cosmid library (Clontech, Palo Alto, Calif., USA) using the hDRR7 forward primer (CGAATTCCGCCACCATGGATCCAACCAC-CCCGG) (SEQ ID NO:13) and the hDRR7 reverse primer (GCTCTAGAGGCTGTCCATCTCTACACCAGACTGC) (SEQ ID NO:14). The resulting PCR product was inserted into the mammalian expression vector pcDNA3 (Invitrogen, Carlsbad, Calif., U.S.A.) and was used in subsequent screening experiments.

Transient Expression in Mammalian Cells and FLIPR Assay

The hDRR7 expression plasmid was transiently co-transfected with a Gα16-pcDNA3 contruct using the FuGENE 6 reagent (Roche Molecular Biochemicals, Mannheim, Germany) into HEK293 cells. The cells were loaded with Fluo-4 (Molecular Probes, Eugene, Oreg., U.S.A.) according to the recommendations of the supplier. Subsequently the cells were assayed in the FLIPR instrument (Molecular Devices, Sunnyvale, Calif., U.S.A.) for $Ca^{2+}$ transients.

Membrane Preparation

The membranes were prepared as total particulate fractions. The cell lines were cultured to 90% confluency on 145 mm petri dishes and treated with 5 mM sodium butyrate, 24 hours before collection. The culturing medium was removed and the cells were washed twice with ice cold phosphate buffered saline (PBS w/o $Ca^{2+}$ and $Mg^{2+}$), scraped from the plates in 50 mM Tris-HCl buffer, pH 7.4, and collected by centrifugation (10 minutes at 16,000 RPM at 4° C.). The cell pellet was re-suspended in hypotonic 5 mM Tris-HCl buffer, pH 7.4, and homogenized with an Ultra Turrax homogenizer. The homogenate was centrifuged at 18,000 RPM for 20 minutes at 4° C. The final pellet was re-suspended in 50 mM Tris-HCl buffer, pH 7.4 and stored in aliquots at −70° C. A protein determination was performed using the Bradford protein assay (Biorad) using bovine serum albumin (BSA) as standard.

Verify Expression Levels of Genes Via Real-time Quantification PCR

RNA from various tissues was obtained from Clontech except the Dorsal Root Ganglia RNA which was obtained from Analytical Biological Services. SDS primers and TaqMan probes for the hDRR7 gene have been designed using PrimerExpress 1.0 software (Perkin Elmer, Mass., USA). The SDS forward and reverse primers for the hDRR7 gene were 5'-TGGAAATGACCAAGCCCTTCT-3' (SEQ ID NO:15) and 5'-GAAAAGGATCAGGAAGACCGG-3' (SEQ ID NO:16), respectively. The TaqMan probe for hDRR7 (5'-ATCAGGGTCTCCTTGCCACAAAGCAGT-3' (SEQ ID NO:17) has been designed using PrimerExpress 1.0 software (Perkin Elmer, Mass., USA) and can be chosen either from the upper strand or the lower strand of the target sequence. The Tagman hDRR7 probe has been labeled with a reporter fluorescent dye, 6-carboxyfluorescein (FAM) at the 5' end.

cDNA was made using Superscript II Reverse transcriptase. RT was carried out for 60 min at 42° C. in a water bath. The reaction was terminated by heating at 70° C. for 10 min. The PCR amplification was then performed in MicroAmp Optical 96-well reaction plates for 50 cycles with each cycle at 95° C. for 15 s and 60° C. for 1 min. All reactions were carried out in triplicate using the ABI Prism 7700 SDS. Relative expression of hDRR7 in the tested tissues was compared to β-actin expression.

Results

Generation and cDNA Sequence of hDRR7

After performing PCR on a human genomic cosmid library a single PCR products was obtained. Sequencing of the PCR product showed that the sequence was identical to a stretch of sequence in an entry in the EMBL database (AX099247). We arrived at the nucleotide sequence depicted in SEQ ID NO:11.

Effect of the hDRR4 Activating Substance in the Cell Based FLIPR Assay

Figure 4:
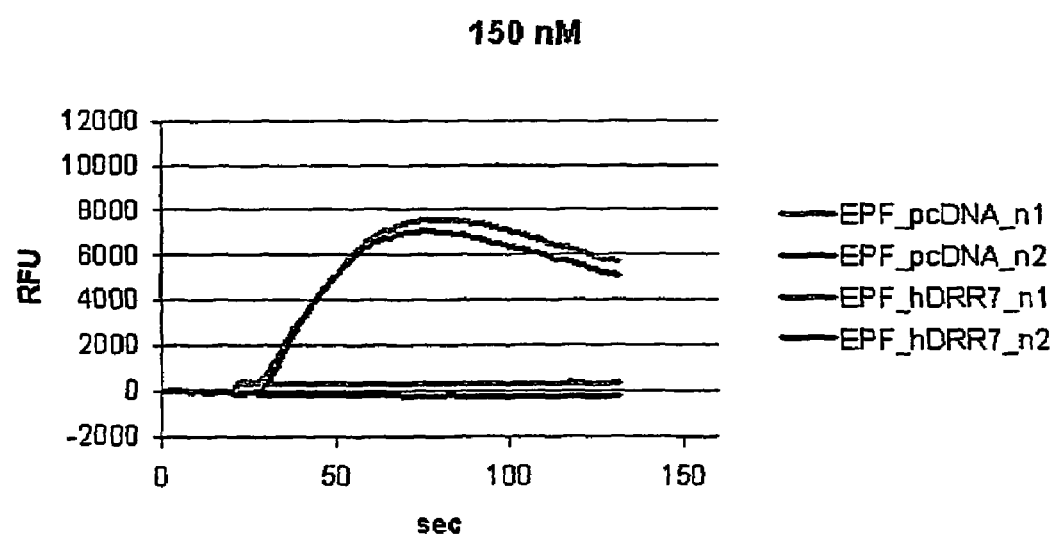
FIG. 4—Activation of orphan GPCR hDRR7 (SEQ ID NO:12) by the hDRR binding fragment of EPF (SEQ ID NO:8) at a test concentration of 150 nM after transient co-transfection with Gα16-pcDNA into Hek293. Relative fluorescence units (RFU) were determined by loading the cells with Fluo-4 (Molecular Probes, Eugene, Oreg., U.S.A.)
Figure 8:
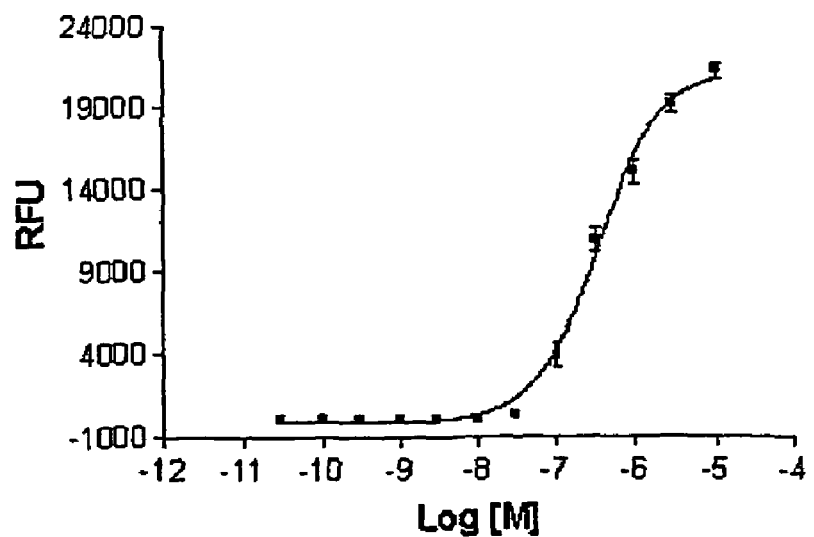
FIG. 8—Dose response curve of the hDRR binding fragment of EPF (SEQ ID NO:8) on the hDRR7 receptor as determined using the FLIPR calcium assay.

Activation of orphan GPCR hDRR7 (SEQ ID NO:12) by the hDRR binding fragment of EPF (SEQ ID NO:8) at a test concentration of 150 nM after transient co-transfection with Gα16-pcDNA into HEK293 cells. Relative fluorescence units (RFU) were determined by loading the cells with Fluo-4 (Molecular Probes, Eugene, Oreg., U.S.A.). Hek 293 cells only transfected with the Gα16-pcDNA expression vector did not response to the hDRR binding fragment as shown in FIG. 4. Using this FLIPR assay at different test concentrations of the hDRR activating peptide consisting of SEQ ID NO:8, an $EC_{50}$-value of 354 nM has been determined (FIG. 8).

Expression of the hDRR7 Gene

Figure 5:
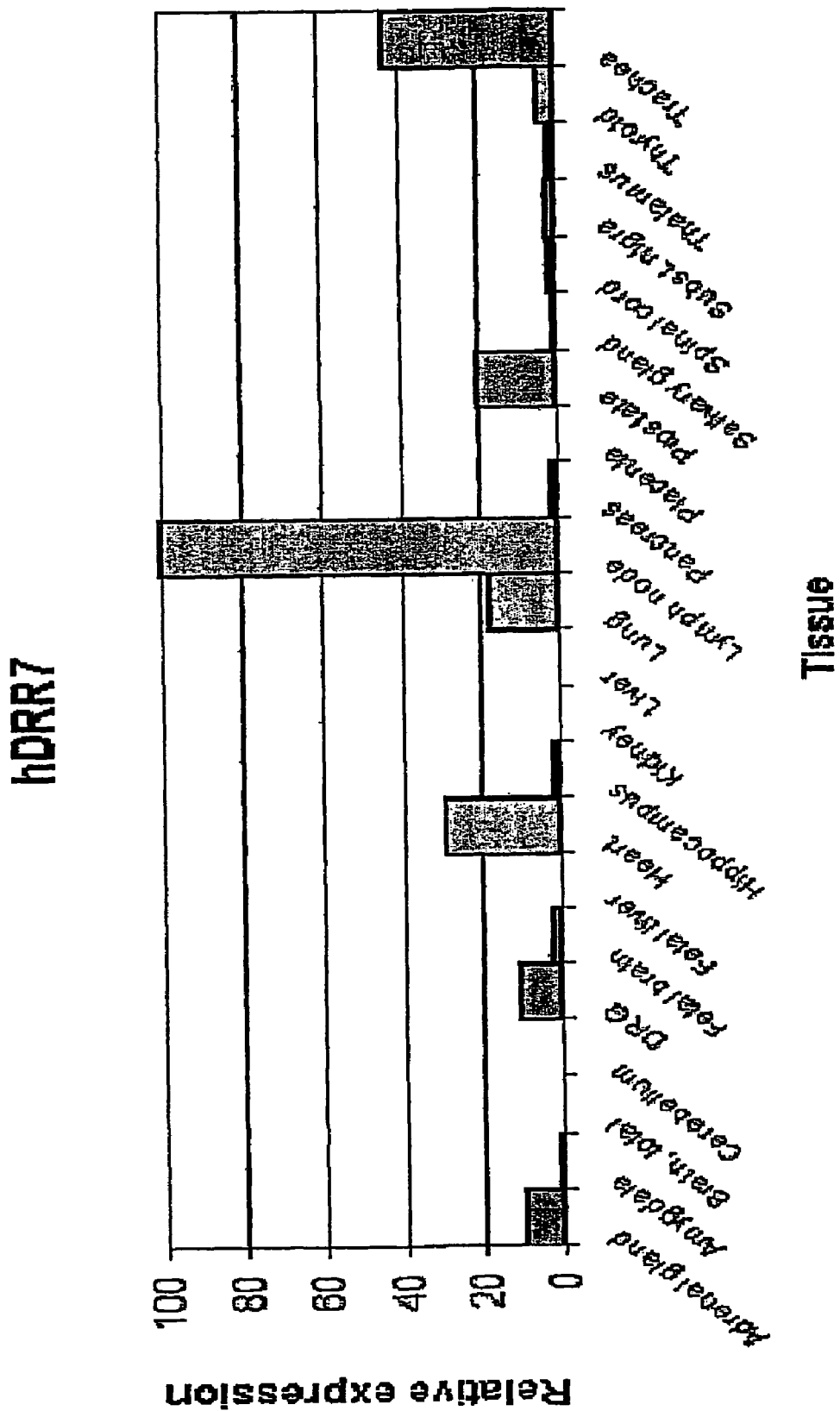
FIG. 5—Relative expression of hDRR7 in a number of tissues compared to the lymph node expression that is taken as 100%. Expression levels were determined using real time quantitative PCR.

Real-time quantification PCR, revealed hDRR7 expression in lymph nodes. This finding, in combination with the identification of early pregancy factor as natural agonist of the hDRR receptors, substantiates the potential role of this receptor in the immunosuppressive action of EPF observed during pregnancy (Davis and Maslow, 1992). Of al the tissues tested, hDRR7 was predominantly expressed in lymph nodes as shown in FIG. 5 wherein the expression levels in the other tissues were compared to the expression level observed in lymph nodes.

EXAMPLE 3

Purification and Identification of EPF-Related Peptides

Material and Methods

Materials

Expand high fidelity polymerase, PCR buffer, T4 DNA ligase, and restriction endonucleases were obtained from Boehringer (Mannheim, Germany). Oligonucleotides were purchased from Eurogentec (Seraing, Belgium). Plasmid preparation kits and the Qiaquick PCR amplification kit were from Qiagen (Hilden, Germany). The PRISM Ready Reaction Dye Terminator Cycle Sequencing kits and the ABI 377 or 373A sequencing machines were from Applied Biosystems (Foster City, Calif., U.S.A.). The Geneamp PCR System 9600 was from Perkin-Elmer (Norwalk, Conn., U.S.A.). The mammalian expression vector pcDNA3 was obtained from Invitrogen (Carlsbad, Calif., U.S.A.). Dulbecco's modified Eagle medium (DMEM), foetal calf serum, and dialysed foetal calf serum was from Life Technologies (Gaithersburg, Md., U.S.A.).

DNA Sequencing

DNA sequencing was carried out with reagents from the ABI PRISM BigDye Terminator Cycle Sequencing Ready Reaction Kit (PE Biosystems) on PTC-200 PCR machines (MJ Research). Reaction products were purified on SEQueaky Kleen 96 well Terminator Removal Kit columns (BioRad) and were resolved on ABI377 DNA sequencing machines. For sequence analysis we used the Sequencher software from GeneCodes (Ann Harbor, Mich.).

Cloning of hDRR4I

PCR was performed on a human genomic cosmid library (Clontech, Palo Alto, Calif. USA) using a forward primer (GGAATTCGCCACCATGGATCCAACG-GTCTCAACCTTGG) (SEQ ID NO: 25) and a reverse primer (GTCTCGAGTCACTGCTCCAATCTGCTTCCC) (SEQ ID NO: 6). The resulting PCT products were cloned with the help of the TOPO™ TA Cloning kit (Invitrogen, Carlsbad, Calif., U.S.A.) The full-length reading frame was inserted into the mammalian expression vector pcDNA3 (Invitrogen, Carlsbad, Calif., U.S.A.) and was used in subsequent screening experiments.

Cloning of hDRR7

PCR was performed on a human genomic cosmid library (Clontech, Palo Alto, Calif., USA) using the hDRR7 forward primer (CGAATTCCGCCACCATGGATCCAACCAC-CCCGG) (SEQ ID NO:13) and the hDRR7 reverse primer (GCTCTAGAGGCTGTCCATCTCTACACCAGACTGC) (SEQ ID NO:14). The resulting PCR product was inserted into the mammalian expression vector pcDNA3 (Invitrogen, Carlsbad, Calif., U.S.A.) and was used in subsequent screening experiments.

Transient Expression in Mammalian Cells and FLIPR Assay

The hDRR4 expression plasmid or the hDRR7 expression plasmid was transiently co-transfected with a Gα16-pcDNA3 construct using the FuGENE 6 reagent (Roche Molecular Biochemicals, Mannheim, Germany) into HEK293 cells. The cells were loaded with Fluo-4 (Molecular Probes, Eugene, Oreg., U.S.A.) according to the recommendations of the supplier. Subsequently the cells were assayed in the FLIPR instrument (Molecular Devices, Sunnyvale, Calif., U.S.A.) for $Ca^{2+}$ transients.

Purification from a Thyroid Gland Extract.

2.5 kg porcine thyroid glands were homogenized and extracted in methanol/water/acetic acid (90/9/1, v/v/v). After centrifugation, the supernatant was delipidated by n-hexane extraction and the aqueous layer was fractionated by a MegabondElute solid phase extraction. The material eluting from 0 to 50% acetonitrile in aqueous trifluoracetic acid (0.1%) was further fractionated by reverse phase HPLC on a preparative DeltaPak C18 column (40×100 mm). The fractions derived thereof were tested for activation of the hDRR4 GPCR in the FLIPR assay. Subsequent purification steps on a preparative Deltapak C4 column (25×10 mm), an analytical C18 column (4.6×250 mm), a narrow bore X-terra C18 column (2.1×250 mm) and finally a capillary Symmetry C18 column (0.32×150 mm) were also followed by the FLIPR based activity assay for fractions activating hDRR4 transfected cells.

Results

Purification of the Natural Agonist of hDRR4 from Porcine Thyroid Glands

Essentially, an extract from the tissue known to be a rich source of secreted peptides, e.g. thyroid gland was prepared and the purification of the natural ligand was followed by a cellular assay based on the activation of the orphan GPCR as described in Material and Methods.

The screening of the porcine thyroid gland extract after the first fractionation on a C18 column delivered a range of fractions that resulted in transient intracellular $Ca^{2+}$ release for cells transiently transfected with the hDRR4 expression construct.

Two adjacent fractions were purified to homogeneity and analysed by ESI-Qq-TOF MS. Both fractions yielded two prominent triple charged ion peaks at m/z 640.59 corresponding to a mass of 1918.77 Da and at m/z 716.63 corresponding to a mass of 2146.89 Da. These peaks were selected in a tandem MS experiment and fragmented by collision-induced dissociation on a Q-TOF system. Four possible sequences were obtained for the 2146.8 Da compound: $LGX_1ARFX_2FLPLFDRVLVE$, ($X_1$ and $X_2$ being K or O) (SEQ ID NOs 18, 19, 26), and four possible sequences for the 1918.77 Da peptide, which is a shorter isoform of the first peptide, $LGX_1ARFX_2FLPLFDRVL$, ($X_1$ and $X_2$ being K or Q) (SEQ ID NOs 20, 21, 27).

The amino acids 2-19 and 2-17 of these sequences correspond to chaperonin10 (Hsp10) 2-18 and chaperonin10 (Hsp10) 2-16 respectively. The amino acid residue on position 7 is a lysine (K) in chaperonins of all vertebrates studied so far. The amino acid residue on position 3 is a Q in *Rattus norvegicus*, *Mus musculus* and *Homo sapiens*, all mammalian species and a K in *Gallus gallus* (Aves).

FLIPR Measurement

Figure 9:
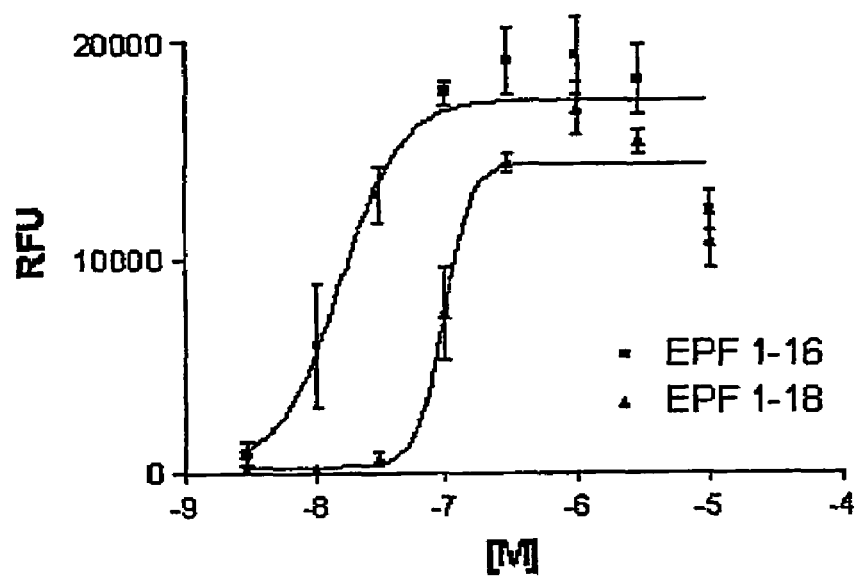
FIG. 9—Dose response curve of the EPF-related peptides EPF1-16 (SEQ ID NO:19) and EPF1-18 (SEQ ID NO:21) on the hDRR4 receptor as determined using the FLIPR calcium assay.
Figure 10:
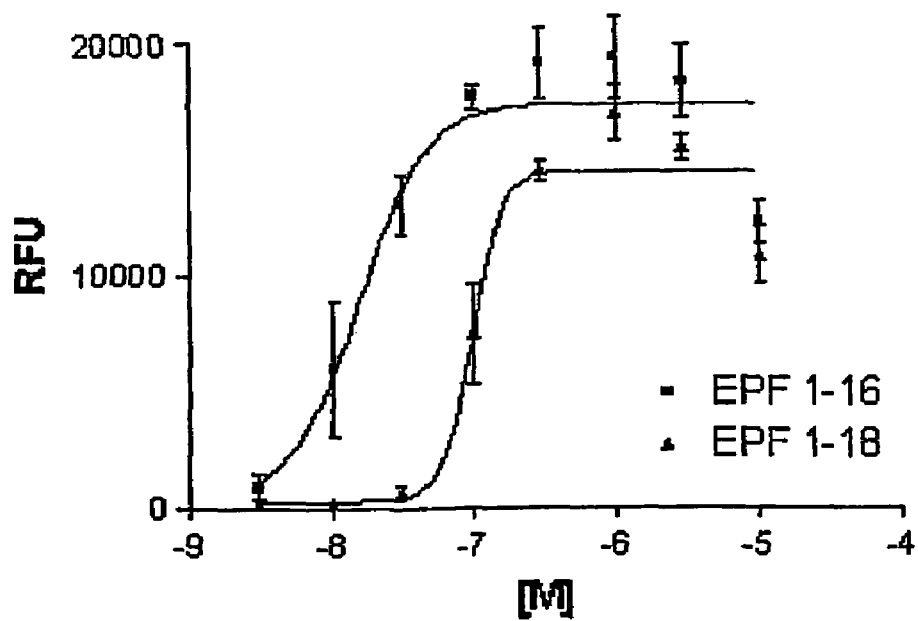
FIG. 10—Dose response curve of the EPF-related peptides EPF1-16 (SEQ ID NO:19) and EPF1-18 (SEQ ID NO:21) on the hDRR7 receptor as determined using the FLIPR calcium assay.

The purified peptides or dried tissue fractions were dissolved in calcium buffer and loaded onto regular multi-well 96 plates. Subsequently the cells were assayed in the FLIPR instrument (Molecular Devices, Sunnyvale, Calif., U.S.A.) for $Ca^{2+}$ transients. For the EPF-related peptides the following $pEC_{50}$ values were determined;

| Name | Sequence | MrgX1 (pEC50) | MrgX2 (pEC50) | |
|---|---|---|---|---|
| EPF 1-16 | LGQAFRKFLPLFDRVL (SEQ ID NO:21) | 7.821 ± 0.1538 | 6.059 ± 0.916 | FIG. 9 |
| EPF 1-18 | LGQAFRKFLPLFDRVLVE (SEQ ID NO:19) | 7.003 ± 0.0462 | 6.086 ± 0.105 | FIG. 10 |

REFERENCES

Altschul, S. F., Madden, T. L., Schaffer A. A., Zhang, J., Zhang, Z., Miller, W., and Lipman, D. J. (1997) Gapped BLAST and PSI-BLAST: a new generation of protein database search programs. *Nuclic Acids Res.* 25, 3389-3402.

Athanasas-Platsis, S., Corcoran, C. M., Kaye, P. L., Cavanagh, A. C., and Morton, H. early pregnancy factor is required at two important stages of embryonic development in the mouse. American J. of Reproductive Immunology 43 (4), 2000, 223-233.

Confavreux, C., Hutchinson, M, Hours, M. M., Cortinovis-Toumiaire, P., and Moreau, T. Rate of pregnancy-related relapse in multiple sclerosis. pregnancy in multiple sclerosis group. New England J. of Medicine 339 (5), 1998, 285-291.

Davis, R. K, and Maslow, A. S. Multiple sclerosis in pregancy: a review. Obstetrical & Gynecological Survey 47 (5), 1992, 290-296.

Hickey, R. W., Zhu, R. L., Alexander, H. L., Jin, K. L., Stetler, R. A., Chen, J., Kochanek, P. M., and Graham, S. H. 10 kD mitochondrial matrix heat shock protein mRNA is induced following global brain ischemia in the rat. Brain Research. Molecular Brain Research 79 (1-2), 2000, 169-173.

Hinuma, S. et al (1998) A prolactin-releasing peptide in the brain. *Nature* 393, 272-276.

Lau, S., Patnaik, N., Sayen, M. R., and Mestril, R. Simultaneous overexpression of two stress proteins in rat cardiomyocytes and myogenic cells confers protection against ischemia—induced injury. Circulation 96 (7), 1997, 2287-2294.

Morton, H. Early pregnancy factor: an extracellular chaperonin 10 homologue. Immunology & Cell Biology 76 (6), 1998, 483-496.

Reinscheid R. K. et al., (1995) Orphanin FQ: A neuropeptide that activates an opioidlike G-protein-coupled receptor. *Science* 270, 792-794.

Sakurai T. et al., (1998) Orexins and orexin receptors: a family of hypothalamic neuropeptide and G-protein-coupled receptors that regulate feeding behaviour. *Cell* 92, 573-585.

Stadel, J. M., Wilson, S., and Bergsma, D. J. (1997) Orphan G protein-coupled receptors: a neglected opportunity for pioneer drug discovery. *TiPS* 18, 430-437.

Summers, K. M., Fletcher, B. H., Macaranas, D. D., Somodevilla-Torres, M. J., Murphy, R. M., Osborne, M. J., Spurr, N. K., Cassady, A. I., and Cavanagh, A. C. Mapping and characterization of the eukaryotic early pregnancy factor/chaperonin 10 gene family. Somatic Cell & Molecular Genetics 24(6), 1998, 315-326.

Tatemoto K, Hosoya M, Habata Y, Fujii R, Kakegawa T, Zou M X, Kawamata Y, Fukusumi S, Hinuma S, Kitada C, Kurokawa T, Onda H, Fujino M. (1998) Isolation and characterization of a novel endogenous peptide ligand for the human APJ receptor. Biochem Biophys Res Commun. 251, 471-476.

Wilson S., Bergsma D. J., Chambers J. K., Muir A. I, Fantom K. G., Ellis C., Murdock P. R., Herrity N. C., Stadel J. M. (1998) Orphan G-protein-coupled receptors: the next generation of drug targets? Br. J. Pharmacol. 125, 1387-1392.

What is claimed is:

1. An isolated and purified hDRR7 binding fragment of EPF of between 16 and 21 amino acids having at least 70% sequence identity with EPF, said fragment being selected from the group consisting of:

a sequence consisting of amino acid sequence SEQ ID NO:8; or

SEQ ID NO:18, SEQ ID NO:19, SEQ ID NO:20 or SEQ ID NO:21; and a sequence comprising the amino acid sequence AFRKFLPLFDRVL (SEQ ID NO: 28).

2. An isolated and purified nucleic acid molecule encoding hDRR7 binding fragment of EPF of between 16 and 21 amino acids having at least 70% sequence identity with EPF, said fragment being selected from the group consisting of:

a sequence consisting of amino acid sequence SEQ ID NO:8;

SEQ ID NO:18, SEQ ID NO:19, SEQ ID NO:20 or SEQ ID NO:21; and a sequence comprising the amino acid sequence AFRKFLPLFDRVL (SEQ) ID NO: 28).

3. A pharmaceutical composition comprising an hDDR7 binding fragment of EPF of between 16 and 21 amino acids having at least 70% sequence identity with EPF, said fragment being selected from the group consisting of SEQ ID NO: 8, SEQ ID NO:18, SEQ ID NO:19, SEQ ID NO:20 or SEQ ID NO:21 and a sequence comprising the amino acid sequence AFRKFLPLFDRVL (SEQ ID NO:28).

4. A pharmaceutical composition for the treatment of autoimmune diseases or other conditions where immunosuppressive actions are desired or to prevent transplant rejection, wherein the pharmaceutical composition comprises the hDRR7 binding fragment of EPF of between 16 and 21 amino acids having at least 70% sequence identity with EPF, said fragment being selected from the group consisting of SEQ ID NO:8, SEQ ID NO:18, SEQ ID NO: 19, SEQ ID NO: 20 and SEQ ID NO: 21 or a sequence comprising the amino acid sequence AFRKFLPLFDRVL (SEQ ID NO: 28).

5. The pharmaceutical composition of claim 4, wherein said autoimmune disease or condition where immunosuppressive action is desired is selected from rheumatoid arthritis, multiple sclerosis and Inflammatory Bowel Disease (IBD).

* * * * *